US007059206B1

(12) United States Patent
Kingston et al.

(10) Patent No.: US 7,059,206 B1
(45) Date of Patent: Jun. 13, 2006

(54) AQUATIC PASSIVE SAMPLING DEVICE AND METHODS FOR ITS USE

(75) Inventors: Jenny Kingston, Portsmouth (GB); Richard Greenwood, Portsmouth (GB); Graham Mills, Portsmouth (GB); Gregory Mark Morrison, Sollebrunn (SE); Lena Bodil Bjoerklund Persson, Moelndal (SE)

(73) Assignee: University of Portsmouth (GB)

( * ) Notice: Subject to any disclaimer, the term of this patent is extended or adjusted under 35 U.S.C. 154(b) by 0 days.

(21) Appl. No.: 10/069,351

(22) PCT Filed: Aug. 25, 2000

(86) PCT No.: PCT/GB00/03300

§ 371 (c)(1),
(2), (4) Date: Jul. 11, 2002

(87) PCT Pub. No.: WO01/14852

PCT Pub. Date: Mar. 1, 2001

(30) Foreign Application Priority Data

Aug. 25, 1999 (GB) ................................ 9920170.9

(51) Int. Cl.
*G01N 1/00* (2006.01)
(52) U.S. Cl. .................... 73/863.23; 73/64.56
(58) Field of Classification Search .............. 73/64.41, 73/64.43, 64.44, 64.47, 64.53, 863.23, 53.01, 73/61.61, 61.63, 61.71, 61.73, 61.41, 61.43, 73/61.44, 64.63
See application file for complete search history.

(56) References Cited

U.S. PATENT DOCUMENTS

| 4,092,117 A | * | 5/1978 | Byrne ........................ 436/73 |
| 4,614,575 A | * | 9/1986 | Juda et al. ................... 204/265 |
| 4,632,746 A | * | 12/1986 | Bergman ..................... 204/415 |
| 4,923,586 A | * | 5/1990 | Katayama et al. ..... 204/403.05 |
| 5,071,610 A | * | 12/1991 | Hagen et al. ............... 264/120 |
| 5,167,823 A | * | 12/1992 | Leighton et al. ........... 210/637 |
| 5,279,742 A | * | 1/1994 | Markell et al. ............. 210/638 |
| 5,328,758 A | * | 7/1994 | Markell et al. ............. 442/351 |
| 5,375,477 A | | 12/1994 | Neill et al. |
| 5,391,298 A | * | 2/1995 | Pieper et al. ............... 210/638 |
| 5,454,951 A | * | 10/1995 | Hoopman .................... 210/650 |

(Continued)

FOREIGN PATENT DOCUMENTS

GB     1 566 253     4/1980

(Continued)

OTHER PUBLICATIONS

Verhaar et al.; "Surrogate Parameter for the Baseline Toxicity Content of Contaminated Water: Simulating the Bioconcentration of Mixtures of Pollutants and Counting Molecules;" Environmental Science & Technology, vol. 29, No. 3, pp. 726-734, (1995).

(Continued)

*Primary Examiner*—Charles Garber
*Assistant Examiner*—Rodney Frank
(74) *Attorney, Agent, or Firm*—Finnegan, Henderson, Farabow, Garrett & Dunner, L.L.P.

(57) ABSTRACT

An aquatic passive sampling device is disclosed comprising a diffusion-limiting membrane and a receiving phase itself comprising an immobilised solid phase material supported by a solid support. The solid support and membrane features enable the device to be adapted for use forcontinuously monitoring a variety of micropollutants, including polar organic, non-polar organic and inorganic analytes. Furthermore, the analytes may be collected by short column extraction rather than batch extraction.

68 Claims, 5 Drawing Sheets

U.S. PATENT DOCUMENTS

| | | | | |
|---|---|---|---|---|
| 5,552,053 A | * | 9/1996 | Ho et al. | 210/640 |
| 5,603,953 A | * | 2/1997 | Herbig et al. | 424/473 |
| 5,689,059 A | * | 11/1997 | Oh et al. | 73/23.31 |
| 5,703,359 A | | 12/1997 | Wampler, III | |
| 5,804,743 A | | 9/1998 | Vroblesky et al. | |
| 5,834,633 A | * | 11/1998 | Davison | 73/53.01 |
| 6,099,804 A | * | 8/2000 | Clausen et al. | 204/403.09 |

FOREIGN PATENT DOCUMENTS

| | | |
|---|---|---|
| GB | 2 295 229 | 5/1996 |
| WO | WO 93/01494 | 1/1993 |
| WO | WO 94/20192 | 9/1994 |
| WO | WO 95/05591 | 2/1995 |
| WO | WO 98/41838 | 9/1998 |

OTHER PUBLICATIONS

Wong et al.; "Multi-Laboratory Evaluation of the Analytical Methodologies from EPA's Bioconcentration Draft Guidance," Second Society of Enviromental Toxicology and Chemistry World Congress—Abstract Book; p. 215, (1995).

Mattice et al.; "Potential Passive Empore C18 Disk Extraction for Analysis of Water Samples Containing Fine Particulates;" Bulletin of Environmental Contamination and Toxicology, vol. 60, pp. 202-208, (1998).

Meadows et al.; Estimation of Uptake Rate Constants for PCB Congeners Accumulated by Semipermeable Membrane Devices and Brown Trout (*Salmo trutta*); Enviromental Science & Technology, vol. 32, No. 12, pp. 1847-1852, (1998).

Sabaliūnas et al.; "Use of Semipermeable Membrane Devices for Studying Effects of Organic Pollutants: Comparison of Pesticide Uptake by Semipermeable Membrane Device and Mussels"; Enviromental Toxicology and Chemistry, vol. 17, No. 9, pp. 1815-1825 (1998).

Frantz et al.; "Permeation Sampling of Halogenated Ether Priority Pollutants"; J. Environ. Sci. Health, A33(7), pp. 1275-1290 (1998).

DeVita et al.; "Quality Control Associated With Use of Semipermeable Membrane Devices"; Environmental Toxicology and Risk Assessment, pp. 237-245 (1999).

Booij et al.; "Calibrating the Uptake Kinetics of Semipermeable Membrane Devices Using Exposure Standards"; Environmental Toxicology and Chemistry, vol. 17, No. 7, pp. 1236-1245, (1998).

Gale; "Three-Compartment Model for Contaminant Accumulation by Semipermeable Membrane Devices"; Environmental Science & Technology, vol. 32, No. 15, pp. 2292-2301 (1998).

Prest et al.; "Validity of Using Semipermeable Membrane Devices for Determining Aqueous Concentrations of Freely Dissolved PAHS"; Environmental Toxicology and Chemistry, vol. 17, No. 4, pp. 535-537, (1998).

Davison; "Device For Concentrating Trace Components In A Liquid" Abstract for United Kingdom Patent Application No. 2 295 229, (1996).

Agata Kot et al., "Passive Sampling for Long-Term Monitoring of Organic Pollutants in Water," Trends in Analytical Chemistry, vol. 19, No. 7, pp. 446-459 (2000).

DiGiano, Francis A., et al., "Application of Passive Dosimetry to the Detection of Trace Organic Contaminants in Water," Environ. Sci. Technol., vol. 22, No. 11, pp. 1365-1367 (1988).

* cited by examiner

AQUATIC PASSIVE SAMPLING DEVICE AND METHODS FOR ITS USE

The present invention relates to a device for the passive sampling of aquatic environments, its construction and use thereof in monitoring trace constituents in aquatic environments. In particular, this invention relates to a device comprising a receiving phase for the trace constituents that is separated from the aquatic environment by a diffusion-limiting membrane, by which is meant that the rate of accumulation of the trace constituents in the receiving phase is determined by the rate of movement through the membrane by diffusion. In other words, the rate of accumulation is reduced with the membrane present when compared with the rate observed in the absence of the membrane.

The desire to monitor trace constituents arises out of environmental concerns and the need to determine whether aquatic sources are polluted. Often, the trace constituents will be present only at the very limits of detection. However, by means of the device and method according to the present invention, these can be concentrated in the device for a predetermined period of monitoring to provide useful information regarding pollutant levels over time. In the text which follows, the term "micropollutants" will be used to denote such trace constituents. However, it will be understood by persons skilled in the art that the present invention is equally applicable to the detection and determination of trace constituents which are regarded as beneficial and hence might not qualify to be designated as pollutants.

The monitoring of environmental waters for the presence of toxic inorganic (eg heavy metal) and organic micropollutants is a requirement of both domestic and European legislation. The purpose of this monitoring programme is two-fold: both for the assessment of long-term trends in pollutant levels and as a means of recording short-term or episodic periods of increased analyte concentration ("pollution events"). In either case, a technique is required for representatively sampling the aquatic environment that accounts for fluctuations of analyte concentration over time. Considerable spatial and temporal variations are known to exist at particular sampling sites, and the infrequent sampling of aqueous aliquots can lead to significant inaccuracies in the estimation of time-averaged concentrations. In addition, the monitoring of sometimes very low levels of pollutants in the environment is technically very difficult using current technology.

In order to assess the long-term trends in pollutant levels, therefore, a technique is required for the continuous and quantitative isolation of target analytes from the aquatic environment. This would not only allow for the accurate assessment of time-averaged concentrations to be made but would also provide a means of detecting the short-term elevations in levels found in pollution events. The term "continuous" is used in this context to mean that the sampling device is left at the sampling site of interest for a predetermined length of time without user intervention and without regard to changes in the flow of the aquatic medium past the device. For example, the device may be used to monitor micropollutants in an intermittent stream, but this would still be regarded as continuous monitoring. Similarly, a flow of environmental water might be interrupted for a spell during the monitoring period. Nevertheless, the monitoring would still be continuous. The duration of the monitoring period may be any desired period of time suitable for particular circumstances. It may, for example, range from a few hours, through days, to several weeks or even longer depending on the nature of the monitoring exercise.

Hitherto, the technique most commonly used for the monitoring of micropollutants in the aquatic environment is a programme of direct sampling of aqueous media. Possible pollutants are identified according to regional usage patterns, and representative samples are taken from specific sampling points at specific time intervals. The samples are then transported to an analytical laboratory for pre-concentration and instrumental analysis. For example, for the sampling of metal species, solid-phase extraction on $C_{18}$ bonded silica cartridges or disks by filtration has been used, as described by Björklund and Morrison in Analytica Chimica Acta 343 259–66 (1997). This technique allows for the accurate determination of specific compounds in a particular place and at a particular time. The results from these sampling events are correlated and used for the assessment of long-term trends in pollutant levels. However, in order to extrapolate these data successfully and thus to determine the true time-integrated pollutant levels accurately, samples must be taken with sufficient frequency that fluctuations in concentrations around the mean level can be accurately measured. Sampling programmes, therefore, are time-consuming, expensive and labour-intensive, and they have drawbacks in situations where large spatial or temporal variations in pollutant levels are observed. In addition, maintaining sample integrity during storage of samples prior to analysis is also problematic. Alterations in the sample over extended storage periods, even at low temperature, can result in an apparent reduction in analyte concentration.

To try to overcome the problems of sampling, another technique, known as bio-monitoring, is also used. Bio-monitoring is based on the ability of aquatic organisms to accumulate pollutants in their body tissues. Hydrophobic pollutants, in particular, can accumulate to levels that far exceed those found in the surrounding aquatic environment. This process is both active (by means of ingestion of contaminated material) and passive (by means of diffusion of compounds from the aqueous environment through membranes of the body or gills into the lipid tissues of their bodies).

Bio-monitoring studies make use of this process to monitor low-level contamination in aquatic environments. Aquatic organisms, usually bivalve molluscs, are exposed at specific sampling sites and the extent of accumulation of pollutant compounds in their body tissues is measured. Compounds in the organism become concentrated to levels far exceeding those found in the aquatic environment, which allows for ng/l levels of contaminants to be determined without the need for very large sample volumes to be analysed. As bio-monitoring is an accumulative process, it effectively provides a means for the continuous, in-situ sampling of lipophilic organic analytes and metal species throughout the period of deployment, thereby providing information on the fluctuating analyte concentrations to which the organisms have been exposed.

However, the drawbacks of using aquatic organisms for monitoring levels of micropollutants include: The handling of tissue samples is time-consuming and may require extensive clean-up prior to analysis. The choice of organism used for bio-monitoring surveys is important; a single bio-monitoring species will be restricted to a particular climate and water type, and all species are unsuitable for deployment in highly polluted sites where the survival rate of the test organisms is low. As bio-concentration is basically a partitioning process between the aqueous environment and the lipid tissues of the organism used, variations in percentage fat in each individual will alter the rate of accumulation. Rates of bio-accumulation also vary widely between individuals of different species and are also significantly affected by age, sex and general health of the test organism. In addition to the large inter- and intra-species variation in accumulation rates, some organic materials can be metabolised by certain organisms (e.g. many polyaromatic hydrocarbons are metabolised rapidly in the tissues of fish but not in the tissues of bivalve molluscs).

Attempts have therefore been made to develop techniques that exhibit the advantages of bio-monitoring but without the above-mentioned disadvantages. Therefore, wholly passive (i.e. not requiring added energy) sampling devices have been developed in an attempt to provide an integrative technique for continuously monitoring aqueous contaminant levels without the drawbacks of using living organisms or expensive electrically-powered equipment. Current systems include those comprising a liquid or liquid-containing receiving phase having a high affinity for micropollutants that is separated from the aquatic environment by a porous membrane. They rely on the partitioning of pollutant species from the aqueous phase to the receiving phase by means of diffusion through the membrane.

The possible advantages of such systems are two-fold: First, they provide a means of continuously monitoring the levels of pollutants in the aquatic environment, thus providing information on fluctuating analyte concentrations. Secondly, pollutants are accumulated in the receiving phase to levels exceeding those in the environment, thereby enabling very low levels of contaminants to be determined.

By controlling the dimensions and materials used in the design of a particular device, the kinetics of uptake of micropollutants species within the sampler may be controlled. This partitioning behaviour has been related to the physico-chemical parameters of particular compounds. It may be possible, by calibrating a test set of compounds in laboratory experiments, to develop a model which can be used to predict the uptake kinetics of an uncalibrated analyte based on its known physico-chemical parameters. This would render time-consuming calibrations for each pollutant unnecessary.

Various devices have been proposed for use in a passive sampling system. For example, GB patent specification no. 1 566 253 discloses a device comprising a glass vessel containing a non-polar solvent separated from the aquatic environment by means of a porous membrane. This device relies on the passive partitioning of freely dissolved organic micropollutants from the aqueous environment through the porous membrane, such as cellulose, into a hydrophobic receiving phase, such as n-hexane.

However, the majority of known passive samplers for organic compounds make use of a liquid organic receiving phase held within a bag composed of flexible dialysis or polymeric membrane materials. For example, a development of the glass device, where the cellulose dialysis membrane is in the form of a bag filled with n-hexane, is described by Södergren in Environ. Sci. Technol. 21 855–859 (1987). This system has been used by a number of researchers for the accumulation of lipophilic pollutants in laboratory and field trials.

An alternative design based on a non-porous polymeric enclosure or envelope ('bag') is disclosed in U.S. Pat. No. 5,098,573, and comprises a bag made from, for example, polyethylene filled with high molecular mass organics, such as the artificial lipid triolein (1,2,3-tri[cis-9-octadecenoyl] glycerol). This system, again, relies on passive diffusion of organic pollutants through, for example, a diffusion-limiting low-density polyethylene membrane and accumulation in the triolein reservoir. The rate of diffusion of non-polar organic species through low-density polythene material has been said to mimic the diffusion of the same species through biological membranes. The aim of this design compared to that of the n-hexane-filled dialysis bag, therefore, is more closely to imitate the passive uptake of organic pollutants in aquatic organisms. However, a drawback of this system is that analytes need to be extracted from the triolein and concentrated, prior to analysis.

Another approach has been proposed, by Frantz and Hardy in J. Environ. Sci. Health, A33(7) 1275–90 (1998), for the determination of halogenated ether pollutants using time-weighted-average concentrations of the pollutants. Their sampler comprised a glass tube having, at one end, a silicone polycarbonate membrane affixed with silicone cement and sealed at the other end with an aluminium foil-covered rubber stopper. Tenax (registered trademark), a porous polymer based on 2,6-diphenyl-p-phenylene oxide, was placed inside the sampler, which was then exposed to a stirred solution of the pollutants in an exposure tank having an aluminium lid for holding the sampler. However, such a device could not be expected to operate satisfactorily under field conditions in which, inter alia, the air in the glass tube would render the sample buoyant and likely to invert under turbulent conditions, thereby creating a substantial diffusion gap between the polycarbonate membrane and the Tenax; in any event, the Tenax would be capable of substantial movement. Furthermore, analysis thereof is rendered difficult by having to draw off the polluted extractant after the desorption step; and sealing of the polycarbonate membrane to the body of the sampler (the glass tube) also renders this impractical for repeated washing and re-use.

Therefore, despite various improvements resulting from these passive sampling devices, there are still important deficiencies that require to be remedied. They are fragile and depend on the accumulation of analytes in a mobile receiving phase. This mobile receiving phase, in many designs, is prone to leaching from the system, making them unsuitable for deployment in environmentally sensitive areas.

An alternative device, aimed primarily at measuring trace metal concentrations in an aqueous environment, comprises means providing a diffusion pathway, the pathway being or containing a liquid and having a length of at least 0.1 mm, a liquid impermeable barrier such that only one end of the diffusion pathway contacts the liquid environment, and a material in contact with the diffusion pathway at its end remote from the liquid environment and adapted to bind component which has diffused along said pathway characterised in that the said material is an immobile material provided as a layer.

This device is disclosed in British patent specification no. GB 2 295 229. However, this disclosure focuses on the use of the device for inorganic, especially metal, species in which the diffusion pathway is a water-containing gel, eg a polyacrylamide gel, and the binding material is eg a Chelex resin incorporated into the gel. This is not suitable for use in sampling organic analytes, due not least to the difficulty of extracting the analyte from the gel. Even were the binding material to comprise a $C_{18}$ adsorbent instead of the Chelex resin, nevertheless, the device would not be suitable, particularly for non-polar organic analytes that would have difficulty in diffusing through the gel due to their comparative insolubility in water.

Furthermore, in use, the device has certain disadvantages in terms of handling and preparation for use, such as the requirement to hydrate the gel for 24 hours prior to use to ensure dimensional stability; the embedding of the resin in a separate gel as a single plane of close-packed beads; and the necessity to extract the analyte from the gel prior to analysis. In addition to these disadvantages, the combined thicknesses of the various layers used mean that the device is larger than ideal, due to the requirement that the length of the diffusion pathway should be greater (preferably by a factor of 10, more preferably at least 20) than the thickness of the diffusion boundary layer, and is therefore always greater than 0.1 mm and preferably 0.2 to 5 mm.

Therefore, it can be seen that, despite various attempts to provide suitable systems for passive sampling, there are still problems relating to ease of use, analysis and handling; and no system yet can conveniently be adapted to handle a wide variety of analytes, namely both polar and non-polar organic pollutants, as well as inorganic species. Furthermore, some systems have inadequate protection against biofouling of the membrane surface. The biofouling of the membrane alters the uptake kinetics of the system, rendering laboratory calibrations invalid. Still further, in some cases, it has been found that the uptake kinetics of the system are affected by turbulence. Accordingly, the present invention provides a device for monitoring micropollutants in an aquatic environment, which device comprises:

(a) a diffusion-limiting membrane capable of being in contact with the aqueous environment when the device is in use and adapted to allow rate-limited diffusion therethrough of the micropollutants; and, (b) separated from the aqueous environment by the membrane, a receiving phase having a sufficiently high affinity for the micropollutants for receiving and retaining the micropollutants characterised in that the receiving phase comprises an immobilised solid phase material supported by a solid support.

For the avoidance of doubt, by 'solid support' in this context is meant a support that is a homogenous solid. Therefore, the solid support for use in the device according to this invention does not contain or retain water within its structure and can not exchange water with its environment. Therefore, the solid support is not subject to loss of water and hence changes in dimension, due either to evaporation or osmotic flux. The solid phase material is therefore supported by, rather than contained or retained within, the solid support. The receiving phase of the present invention is accordingly mechanically strong and structurally inert. Preferably, the solid phase material is immobilised by being bound in or to a hydrophobic solid support material, such as a matrix of hydrophobic fibres, as described further hereinbelow.

Therefore, the present invention provides a device wherein the receiving phase is in a form that is relatively rigid, unlike the liquid, powder, granular or gel-based forms used in prior art devices. Such devices provide the additional advantage of being re-usable in that the receiving phase is maintained in its integrity even after analysis. The devices of this invention preferably comprise an immobilised non-polar, chromatographic and/or chelating receiving phase separated from the aqueous environment by means of a diffusion limiting membrane, whereby, in use, dissolved analytes pass through the membrane, across a fixed and substantially constant diffusion gap (effectively the thickness of the membrane) to the hydrophobic chromatographic and/or chelating phase, where they are retained until desorbed.

Accordingly, in another aspect, the present invention provides a device for monitoring micropollutants in an aquatic environment, which device comprises:

(a) a diffusion-limiting membrane capable of being in contact with the aqueous environment when the device is in use and adapted to allow rate-limited diffusion therethrough of the micropollutants; and, (b) separated from the aqueous environment by the membrane, a receiving phase having a sufficiently high affinity for the micropollutants for receiving and retaining the micropollutants characterised in that the receiving phase comprises an immobilised solid phase material in association with a solid carrier therefor, which carrier does not contain or retain water within its structure and can not exchange water with its environment, whereby the solid support is not subject to loss of water and hence changes in dimension, due either to evaporation or osmotic efflux.

The solid support or substrate for the solid phase material may comprise any inert, solid material that is resistant to commonly-used extraction solvents; that can maintain integrity in an aquatic environment for economic periods of time; and that can help to prevent damage to the solid receiving phase in use.

Preferred is when the solid support allows free circulation of the medium (such as extraction solvent), used for extracting the micropollutants, around the immobilised solid phase material. Much preferred is when at least one face of the solid support has pores, which allow extraction solvent applied to the opposite face to flow therethrough. This enables extraction of the analytes to be performed quickly by short column, rather than by prolonged batch extraction or leaching, which is described in more detail hereinbelow.

The support may itself be integral with the receiving phase or with a body encompassing the device, or it may comprise a separate component that can be fitted to the body or otherwise adapted to provide support to the receiving phase.

Preferably, the receiving phase is adapted to be maintained, in use, in close proximity to the diffusion-limiting membrane such that there is maintained a substantially zero diffusion gap between the two components. More preferably, in use, the diffusion-limiting membrane is laid directly over the receiving phase and is in contact therewith over substantially the entire area of their opposed faces. Suitably, the receiving phase is less than about 1 mm thick, such as about 0.75 mm thick. In any case, it is preferred that any diffusion gap is less than about 1 mm and more preferably is substantially equal only to the thickness of the membrane.

In the device according to the present invention, the membrane is preferably chosen such that the diffusion pathway (and therefore membrane thickness) is less than 0.2 mm, preferably less than 0.1 mm and is suitably in the range of from 0.02 to 0.15 mm, such as 0.03 to 0.1 mm. Preferably, the thickness of the diffusion-limiting membrane should not generally exceed the thickness of the diffusion boundary layer (ie the unstirred boundary layer which separates the bulk phase of the environment from the surface of the diffusion-limiting membrane) under stagnant or unstirred conditions.

Such limitations on the thickness of the membrane provide for a more rapid sampling rate, and a device according to this invention is therefore more sensitive in its measurements than devices comprising diffusion-limiting membranes of similar surface area wherein the diffusion pathway substantially exceeds the diffusion boundary layer in thickness.

The membrane itself may be a separate component from the receiving phase, or may be integral therewith, such that it is ordinarily inseparable from the receiving phase and may comprise a layer thereof, whether by surface coating or impregnation, or the like.

In order to be suitable for use in sampling for non-polar organic analytes, the device according to the invention is preferably one wherein the diffusion-limiting membrane comprises a substantially non-porous solid, such as a polymeric material that is hydrophobic and not capable of being significantly hydrated, and neither is nor contains a liquid (such as the aqueous environment being monitored) during use. In such devices, the uptake of the analyte(s) is determined by the rate of diffusion through the polymer itself and is not determined by rate of diffusion through a liquid, as is the case with certain prior art devices.

Suitable polymers for use in devices for sampling non-polar organic analytes include polyethylene and polyvinyl chloride. Other suitable polymers, such as non-porous polysulphone or the like, may be used, in which the water content of the membrane is less than about 50%, preferably in the range of from 0 to 30%, more preferably in the range of from 0 to 20%, such as less than about 15%, but more usually less than about 1% or even less than 0.1%. Any pores that may be present in the chosen polymer should be such as not to result, in use, in any significant diffusion through any liquid that may be present in such pores.

Accordingly, in another aspect, the present invention provides a device for monitoring non-polar, organic micropollutants in an aquatic environment, which device comprises:

(a) a diffusion-limiting membrane capable of being in contact with the aqueous environment when the device is in use and adapted to allow rate-limited diffusion therethrough of the micropollutants; and, (b) separated from the aqueous environment by the membrane, a receiving phase having a sufficiently high affinity for the micropollutants for receiving and retaining the micropollutants characterised in that the receiving phase comprises an immobilised solid phase material and the diffusion-limiting membrane comprises a solid, hydrophobic polymeric material capable of determining rate of diffusion of the micropollutants therethrough.

Most preferably, the polymeric material contains less than 1% water and/or is substantially non-porous, whereby the diffusion pathway comprises the solid polymer itself and not any water contained therein. Especially preferred, particularly for sampling non-polar organic micropollutants having log P (or log $K_{ow}$)<4, is polyethylene, further details of which are given in Table 1, hereinbelow.

Preferably, the solid receiving phase for use in the devices according to this invention is a unitary element adapted to be placed directly in a stream of desorbent, from which the desorbent plus micropollutants can be eluted and collected in one step. Instead or as well, the solid receiving phase is adapted to be placed directly in analytical equipment, such as gas chromatography, atomic absorption, mass spectrometry or laser ablation equipment.

Accordingly, in another aspect, the present invention further provides a method for monitoring micropollutants in a polluted environment, which method comprises:

(a) providing a receiving phase comprising an immobilised solid phase material for the micropollutants, which material is supported by a solid support;

(b) providing a diffusion-limiting membrane adapted to allow rate-limited diffusion therethrough of the micropollutants and, in use, adapted to separate the receiving phase from the polluted environment;

(c) bringing the membrane into contact with the polluted environment for a sufficient period of time to allow the micropollutants to collect in the immobilised solid phase material;

(d) removing the solid receiving phase from the environment; and (e) analysing the micropollutants accumulated in the receiving phase.

Preferably the step (e) comprises applying extraction solvent to the receiving phase, whereby the analytes are removed from the receiving phase.

A preferred method of the invention is wherein the solid receiving phase is removed from the environment and is further removed from the device; eluted with a desorbent or extraction solvent for desorbing the micropollutants therefrom; and the eluate analysed.

Preferably, the solvent is applied to one face of the receiving phase and is collected, containing the micropollutant analyte(s), at the opposite face. This process is equivalent to short-column elution, which results in more efficient recovery (approximately 100%) of analyte(s) from the receiving phase, compared with the less efficient recoveries obtained with batch elution (leaching). In batch elution, the analyte(s) are leached from the receiving phase by prolonged (up to 24 hours) soaking in an appropriate solvent, resulting in about 80% recovery for a range of metals and probably lower, if at all, for organic analytes. But in short column elution, the solvent is passed through the pores of the support material in the receiving phase, thereby achieving efficient extraction within minutes.

Accordingly, the present invention further provides a method for monitoring micropollutants, which method comprises exposing a passive sampling device according to the invention to a micropolluted environment for a period of time, thereafter removing the receiving phase having micropollutants bound thereto from the environment and subjecting the receiving phase to short-column elution.

The device is preferably calibrated under a wide variety of conditions for a test-set of analytes with a range of physico-chemical properties. The device and method of the invention are suitable for testing for and monitoring the presence of both organic analytes and inorganic analytes, including pesticides, agrochemicals and polychlorinated biphenyls, such as those listed in Table 2 hereinafter; metals, such as copper (eg Cu(I)), zinc, cadmium, lead, arsenic, mercury and chromium (eg Cr (VI)); and other inorganic elements, including nutrients, such as P (eg $PO_4$) and N (eg $NH_4$, $NO_3$). Especially preferred is a device or method according to the invention suitable for monitoring organic micropollutants, particularly non-polar micropollutants. The final, calibrated device therefore provides a means for the quantitative determination of time-averaged levels of analytes in aquatic environments during extended deployment times. It is robust enough to be placed in a wide range of aquatic environments without adversely affecting its performance and is therefore a significant advance in the field of environmental monitoring.

A primary advantage of the device according to the present invention is that it is more easily customised than prior art devices in order to be useful for testing a range of pollutants—whether several at one time or specific, single pollutants.

Choice of the material for the solid receiving phase will therefore depend, inter alia, on the nature of the particular micropollutant to be monitored. The process of uptake in passive sampling systems is basically one of equilibrium partitioning. In the case of organic analytes, for example, non-polar micropollutant molecules have a higher affinity for the organic receiving phase than the surrounding aqueous environment and therefore accumulate in the sampler to levels exceeding those found in the environment. Thus the rate of uptake is controlled by the nature of the diffusion-limiting membrane, but the position of equilibrium and therefore the capacity of the device is governed by the receiving phase.

A range of commercially available, chromatographic materials with different physico-chemical properties can be used in the device. Some of these solid-phase materials have a proven high affinity to non-polar analytes, for example, having been used for the extraction of organic pollutants from aqueous media. It has also been found that non-polar organic compounds stored on hydrophobic, solid-phase materials have increased stability over those stored refrigerated in aqueous samples. Examples of some suitable solid phase materials include hydrophobic chromatographic phases such as organo-silicas (e.g. $C_6$, $C_8$, $C_{18}$ hydrocarbon bonded silicas) and polymers (e.g. poly(styrenedivinylbenzene)), eg those of formulae (I)–(III) below for organic compounds, and chelating (eg iminoacetates) and ion-exchange materials for metallic species.

Some suitable disks for use as the solid receiving phase in the device of the invention are already commercially available, such as disks of silica-based polymer-bonded medium chain length hydrocarbons eg $C_8$ to $C_{18}$ disks (available from 3M), $C_{18}$ cartridges (such as Varian Bond Elut™), and chelating or ion-exchange disks (also from 3M). In these cases, the solid receiving phase is preferably non-polar and is available in combination with a matrix, such as a PTFE fibril or glass fibre matrix, which acts as the solid support or substrate for the solid phase material. Examples of these include PTFE-based $C_{18}$ or $C_8$ disks (3M Empore™) and glass fibre-based $C_{18}$ disks (Supelco Envi-Disk™). Particularly useful are $C_{18}$ Empore™ disks, which comprise octadecyl chain length hydrocarbon groups bonded in a silica-based polymer embedded within a network of PTFE fibrils. Preferred disks are therefore those having a high (about 90% by weight) particle:PTFE ratio, wherein the particles of solid phase material having a particle size of from about 10 to about 60 μm, especially about 40 μm, are immobilised into a densely-packed, highly uniform sorbent bed.

Preferably, the solid receiving phase is immobilised on a backing plate or support plate positioned against the receiving phase on its face remote from the diffusion-limiting membrane, thereby substantially eliminating any air gap between the receiving phase and the aqueous environment,

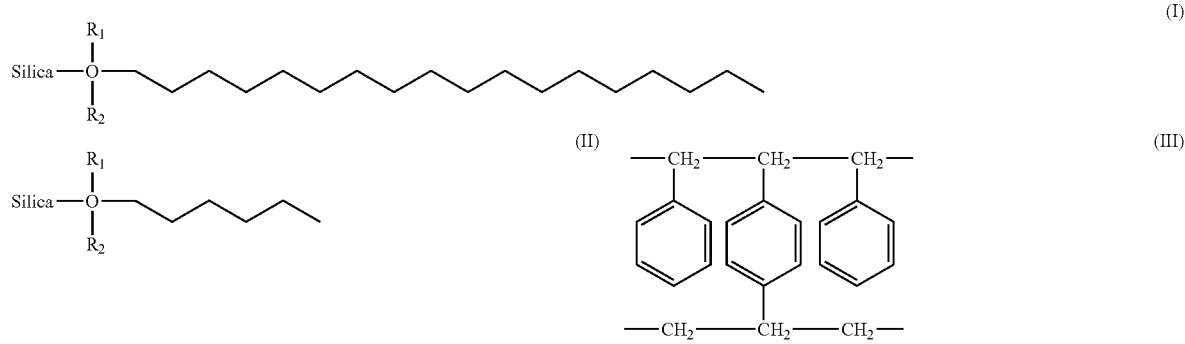

Further advantages are obtained when the solid, receiving phase is in the form of a cartridge or disk, particularly a disk that is suitable for either transfer from the device to a standard filter funnel for removal of the collected analytes or (in the case of metals) direct laser analysis. In this way, the collected micropollutants on the solid receiving phase can be conveniently extracted and measured in the normal way. Such forms of the solid receiving phase (ie disks, cartridges or otherwise wherein the receiving phase itself is intimately associated with a solid substrate) further afford robustness to the device and prevent dispersal into the environment of the receiving phase in the event that damage occurs to the protecting elements of the device (eg the diffusion-limiting membrane).

Particularly where the diffusion-limiting membrane is a separate component of substantially the same shape as the receiving phase or is a layer thereof (eg coating thereon), then these two components of the device are not able to move relative to each other, thereby further preventing damage to the device or the environment, in use. Such a device is thereby fully submersible in aquatic environments. In the case where the diffusion-limiting membrane is integral with the receiving phase, then this may also be coated on or impregnated into the substrate when in use. This is advantageous, as there will be no danger of leakage or loss of receiving phase by means of damage to the device in the aquatic environment.

Therefore, a preferred device according to the invention is one wherein the solid receiving phase is immobilised by being bound in or to a hydrophobic, solid substrate, such as a matrix, which may then itself be immobilised against a backing plate or support. Such support or backing plate may comprise a supporting disk adjacent the receiving phase on its face remote from the diffusion-limiting membrane. Examples of suitable materials for the solid support include high-density polymers, such as high density polypropylene, PTFE or glass fibre.

Accordingly, the method of the invention may further comprise pre-treating the solid receiving phase, such as by coating or impregnating it with the diffusion-limiting membrane; by conditioning it with a conditioner; by treating it with an agent adapted to complex, chelate or otherwise assist the receiving phase to receive and retain the chosen micropollutant, such as a photometric agent; or by loading it with internal standard; or the like; or any combination thereof.

Depending upon the particular solid receiving phase chosen and the pre-treatment applied to it before use, it is possible for the device to be custom-adapted for monitoring one or more analytes at a time. Hence, the solid receiving phase may comprise a chromatographic and/or chelating phase that has been treated with an agent for complexing or chelating the chosen analyte(s), such as metallic species. For example, if $C_{18}$ or $C_8$ disks are used in different matrixes (PTFE, glass fibre) together with a photometric reagent (eg bathocuproine or 1,5-diphenylcarbohydrazide, it is possible to collect specific metal species (eg Cu(I), Cr(VI), respectively). Normally, it is difficult to detect low concentrations of such species with only the photometric reagent bathocuproine, but together with pre-concentration of the metal complexed to a photometric reagent on a $C_8$ or a $C_{18}$ disk, it is possible (as described by Björklund and Morrison ibid). The possibility of having the photometric reagent immobilised on the disk in advance of deployment or to have it directly equilibrated in the sample is also an advantage. Examples of photometric reagents that can be used are bathocuproine, methylthymol blue, xylenol orange, glycine cresol red, binchinonic acid, diphenylcarbazide and 1,5-diphenyl carbohydrazide.

On the other hand, chelating disks may be used to collect a plurality of different metals simultaneously. Alternatively, multivalent metal ions may be collected by treating the matrix (eg chelating resin disk, such as a 3M Empore™ Extraction Disk) with a complexing agent, such as ammonium acetate, so that the receiving phase contains iminoacetate groups that will complex the metal ions.

In some cases, the chosen solid receiving phase (eg in disk form) may require conditioning prior to its use in the device. This conditioning has two effects: it rinses the disk with organic solvent to remove any impurities that may have contaminated the disk during manufacture or storage; and, in the case of use for monitoring organic analytes, it solvates the receiving phase, thereby increasing its ability to sequester any organic analytes to which it may be exposed. For this reason, it is preferred not to allow the disk to dry out at any stage between conditioning and deployment of the passive sampling device. The conditioning process generally comprises soaking the disk in HPLC grade methanol solvent for from about 5 to about 20 minutes at room temperature. During this time the disk may take on a translucent appearance. The disk may then be submerged in ultrapure water to remove excess solvent prior to being removed from the water and dried.

Preferably, the chosen receiving phase is loaded prior to use with an internal standard. By using disks pre-loaded with an internal standard or additional disks so loaded, it is expected that the time-averaged water concentrations of aqueous micropollutants can be calculated more accurately, taking into account alterations in uptake rates due to field variables, such as variations in temperature, turbulence and bio-fouling effects. This internal standard is an isotopically-labelled compound and is designed to diffuse during deployment of the device from the receiving phase through the diffusion-limiting membrane and into the aquatic environment at a known and controlled rate. For example, before use in the sampler, $C_{18}$ receiving phase disks are placed in a vacuum filtration device for loading with internal standard, which preferably comprises $D_8$-naphthalene for a non-polar sampler having a polyethylene membrane or $D_6$-dimethylphthalate for a polar sampler having a polysulphone membrane.

The amounts of internal standard used should be both appropriate for the duration of deployment and also at levels that can be easily measured on the analytical instrument (such as GC/MS, as described in the Examples hereinbelow.). The MS also allows the use of deuterated internal standards that are not naturally occurring environmental pollutants. The internal standard may be made up in water at 1000 ng/100 ml concentration and the whole solution drawn over the disk in the filtration funnel. This results in about 80% (800 ng) of the $D_8$-naphthalene and 100% (1000 ng) of the $D_6$-dimethylphthalate partitioning onto the disk. The loaded disks are then placed in the sampler in the normal way. These gradually off-load internal standard into the water during deployment. The rate of off-loading is predicted and this is affected by the same field variables as the rate of on-loading. Alternatively, these internal standards could be deployed as separate devices.

Alternatively, conservative elements in the aquatic environment, such as Ca and Mg in seawater could be used as naturally-occurring internal standards, since the rate of uptake of these ions would be affected in the same way by field variables as the rate of uptake of other cations such as heavy metals. Since there are much higher levels of these conservative elements present in the environment, their rate of uptake could be measured using patches or small 'ears' or appendages of an appropriate cation exchange material added to existing disks; or deployed as separate devices.

Choice of the material for the diffusion-limiting membrane should be such that the membrane is diffusion-limiting but nevertheless allows the rapid diffusion of analytes through the membrane to provide the system with a rapid response to fluctuating external concentrations. As long as the membrane is truly diffusion-limiting, the rate of uptake will be dependent on environmental concentration rather than on flow rates in the environment. For the avoidance of doubt, a membrane is 'diffusion-limiting' if the rate of accumulation by the receiving phase is determined by the rate of movement (by diffusion) through the membrane, ie the rate of accumulation is reduced when compared with the rate observed in the absence of the membrane.

A range of membrane materials with very different chemical characteristics and physical properties is available for evaluation with regard to their suitability as diffusion-limiting membranes for selected micropollutants in the passive sampling system. A membrane material is required which allows the rapid diffusion of the micropollutant, e.g. small, organic molecules, through either the matrix of the membrane and/or its small pores into the receiving phase of the device. It should also have a low affinity for the micropollutants for which the device is to be calibrated, so that pollutants do not accumulate within the membrane material rather than passing through to the chosen receiving phase. In addition to its diffusional properties, physical robustness and ability to resist bacterial attack should be taken into consideration, as they can be important characteristics of the chosen membrane material in cases where the device is to be deployed in harsh environmental conditions. Examples of suitable membranes for the collection of organic analytes include hydrophilic or hydrophobic polymer materials having a pore size in the range of from about 0.1 µm to 2 µm, such as those listed below in Table 1.

TABLE 1

Example membrane materials suitable for use as diffusion-limiting membranes in the (organics) passive sampling device of this invention.

| Membrane | Dimensions | Manufacturer | Information |
| --- | --- | --- | --- |
| Polycarbonate | 47 mm disk, 0.2 µm pore size | Costar | Chemically inert, hydrophilic material. Pore size of fixed diameter. |

TABLE 1-continued

Example membrane materials suitable for use as diffusion-limiting membranes in the (organics) passive sampling device of this invention.

| Membrane | Dimensions | Manufacturer | Information |
|---|---|---|---|
| Polytetrafluoro-ethylene (PTFE) | 0.5 or 1.0 μm pore size, supplied as sheet material bonded to polypropylene protective backing | Pall Europe | Chemically inert hydrophobic membrane. Requires wetting with suitable solvent prior to deployment. Weak structured membrane supplied with polypropylene backing to provide physical strength |
| Poly-vinyledene-difluoride (PVDF) | 0.2 μm pore size, supplied as sheet material | Pall Europe | Chemically inert hydrophobic membrane. Requires wetting with suitable solvent prior to deployment. Membrane structure sufficiently strong to support itself without protective backing. |
| Low density polyethylene | Flexible polymer, no fixed structure but low polymer crystallinity | Sainsburys, Fisher Scientific | Highly hydrophobic polymeric material. Chemically and biologically resistant. No fixed pore structure. Variety of membrane thicknesses available. |
| Polysulphone | 0.2 μm pore size, supplied in the form of sheet material | Pall Europe | Hydrophobic membrane with fixed pore structure. High chemical and physical resistance. |
| Cellulose dialysis membrane | 1000 MWCO (molecular weight cut-off) dialysis membrane | Millipore | Relatively hydrophilic membrane with fixed pores of universal size. Allows small organic molecules to pass through but forms a barrier to large organic molecules. Low chemical resistance and liable to attack by fouling organisms. |

As described above, for non-polar organic analytes, substantially non-porous polymers such as polyethylene are preferred, where diffusion is primarily through the plastics material and not through pore-held liquid. This material allows the rapid diffusion of non-polar analytes but forms a barrier for the diffusion of relatively polar compounds.

However, for polar organic analytes, such as those having a log P (or log $K_{ow}$)<4, such as a log P in the range of from 2 to 4, preferred diffusion-limiting membranes include polysulphones, whose pores are open to both the internal face of the device and also to the external environment, such that mass flow of solvent could occur were hydrostatic pressure to be applied. This is in distinction from prior art devices involving porous diffusion-limiting materials, which have a seal between the pores and the external environment. The polysulphone membrane as supplied has a high degree of physical strength and is available in a low protein-binding formula, which may also have useful anti-fouling properties.

Accordingly, in a second embodiment, the present invention provides a device for monitoring polar, organic micropollutants in an aquatic environment, which device comprises:
(a) a diffusion-limiting membrane capable of being in contact with the aqueous environment when the device is in use and adapted to allow rate-limited diffusion therethrough of the micropollutants; and,
(b) separated from the aqueous environment by the membrane, a receiving phase having a sufficiently high affinity for the micropollutants for receiving and retaining the micropollutants characterised in that the receiving phase comprises an immobilised solid phase material, and the diffusion-limiting membrane comprises pores traversing the membrane and having a diameter in the range of from 0.1 to 10 μm.

Preferably, the pores have a diameter in the range of from 0.1 to 1 μm, especially about 0.1 to 0.2 μm. Suitable membranes for polar, organic pollutants include polymers such as polysulphone, polycarbonate, cellulose dialysis membrane, PTFE and PVDF, and glass fibre.

Diffusion-limiting membranes particularly suitable for use with inorganic analytes include cellulose acetate (eg 0.45 mm membrane available from Sartorius), GF/C (a glass fibre membrane available from Whatman), nylon membranes (eg available from Sartorius) and dialysis membranes (eg available from Spectrapor). Particularly suitable for such purposes are cellulose acetate membranes.

The diffusion-limiting membrane may also be treated prior to use. For example, to hinder biofouling and to prevent biofouling from becoming a major problem, the surface of the diffusion limiting membrane may be treated appropriately. Biofouling has particularly been reported to affect triolein-filled semi-permeable membrane devices (tubes of low-density polyethylene lay-flat membrane filled with triolein, as described in more detail hereinabove). More problems occur with devices not reliant on solvent since, in solvent-filled devices, leakage of the solvent through the diffusion-limiting membrane hinders colonisation by microorganisms. The extent of biofouling is determined in part by the energy of the surface. Some diffusion-limiting membranes such as the cellulose acetate membranes suitable for use in the inorganic samplers of the present invention are particularly susceptible. Appropriate treatments may include coating or impregnating with an anti-fouling agent, biocide and/or a perfluorinated polymer having pendant sulphonic acid groups, such as Nafion™. Nafion™ (available from Aldrich, UK) provides mechanical strength, is chemically stable and is permeable (to certain molecules, such as charged species). Almost all anions are thereby excluded from the surface of the membrane. Nafion™ is also affected by pH due to its surface charge. Nafion™ comprises sulphonic acid groups ($SO_3^-$) attached to a perfluorinated polymer backbone.

Alternatively, certain silicone elastomers (available from the Department of Chemistry, the University of Portsmouth, UK) can have excellent anti-fouling properties. Non-polar compounds rapidly diffuse across the elastomer surface and therefore either this or Nafion™ itself may comprise the diffusion-limiting membrane, replacing the polyethylene or cellulose acetate or other material. Furthermore, these materials may form an integral unit with the solid receiving phase, such as by forming a layer thereon.

Accordingly, in a third embodiment, the present invention provides a device for monitoring micropollutants in an aquatic environment, which device comprises:

(a) a diffusion-limiting membrane capable of being in contact with the aqueous environment when the device is in use and adapted to allow rate-limited diffusion therethrough of the micropollutants; and, (b) separated from the aqueous environment by the membrane, a receiving phase having a sufficiently high affinity for the micropollutants for receiving and retaining the micropollutants characterised in that the diffusion-limiting membrane is associated with a molecular charge selective material, whereby, in the case of a porous membrane, the kinetics of the diffusion of the analyte through the pores will depend not only on diffusion through the liquid in the pores but also on the interaction of the analyte with the consequent charges associated with the pores. Such membranes are referred to as "permselective" in the text which follows.

Therefore, in this embodiment, there is operating a different mechanism of inorganics sampling, compared with prior art devices: there will occur preferential passive diffusion of metal species with a charge opposite or neutral to that of the fixed exchange sites of the permselective membrane, and/or through molecular size exclusion. The metal concentration gradient across the permselective membrane (between the bulk aqueous phase and the receiving phase surface) provides the driving force for diffusion. The permselective membrane can be designed selectively to permit the transport of specified categories of metal species, and further selectivity can be achieved by choice of receiving phase, as mentioned hereinbefore. Particular advantages of this mechanism include that it avoids matrix interferences and allows pre-concentration of desired metal species to detectable levels.

The permselective membrane assembly preferably constitutes a porous material—such as one of those listed above—selective on the basis of molecular size, and a polymer coating selective on the basis of molecular charge. The molecular charge selective material could be any polymer with ion exchange properties, such as the cationic polymers poly(4-vinylpyridine) and poly(2,6-dimethylphenol), but is preferably the negatively-charged polymer, Nafion™.

It has been found that Nafion™-coated membranes demonstrate, particularly for copper, the effect of preventing the transport of metal-containing colloids to the surface of the receiving phase. As colloidally-bound metals are essentially not bioavailable, the Nafion™ coated membrane gives a separation of metal species on the basis of their charge and size properties, thereby enabling identification of elevated bioavailable concentrations of metals. Therefore, the Nafion™ coated passive sampler functions well in a range of aquatic environments and effectively excludes bulky organic colloids, whose associated metals are essentially non-bioavailable.

In the device according to the invention, the diffusion-limiting membrane and the solid receiving phase together with the solid support may be in contact as an integral, optionally disposable, unit. One or more, and preferably all three, of these essential components of the device according to this invention are preferably placed, prior to use, in a body adapted to receive it/them. Therefore, the present invention further provides a unit for use as a passive sampling device, which unit comprises a device according to the invention and an inert body (which may itself comprise the solid support) adapted to allow insertion therein and removal therefrom of the solid receiving phase and adapted to allow access from the aqueous environment of the micropollutants to the membrane. Examples of suitable materials for the body include high-density polymers, such as high-density polypropylene, PTFE or glass fibre. Preferred is PTFE.

Optionally, the device may further be provided with further mechanical protection, in particular that adapted to provide mechanical protection for the diffusion-limiting membrane. Accordingly, netting such as a polypropylene net or a mesh such as stainless steel mesh may be provided on the face of the membrane away from the receiving phase in order to provide a compact sampler without air in between the receiving phase and the diffusion-limiting membrane; to help prevent any mechanical damage that can occur in the field; and to help prevent large solids or sediment from damaging or contaminating the sampler.

Optionally, the device may further comprise a removable sealing plate to hold in and/or further protect the diffusion limiting membrane during transportation and/or storage. The sealing plate may be held in position in the inert body and/or in relation to the solid support by securing means, such as a screw-threaded ring. The sealing plate may also be adapted to form a cap or stopper to enable water or other conditioning fluid(s) to be maintained in contact with the solid receiving phase, such as to prevent its drying out between preparation and use of the device. Examples of suitable materials for the sealing plate include high-density polymers, such as high-density polypropylene, PTFE or glass fibre. Preferred is PTFE.

The present invention will now be illustrated by way of example only with reference to the following drawings, in which.

Figure 1:
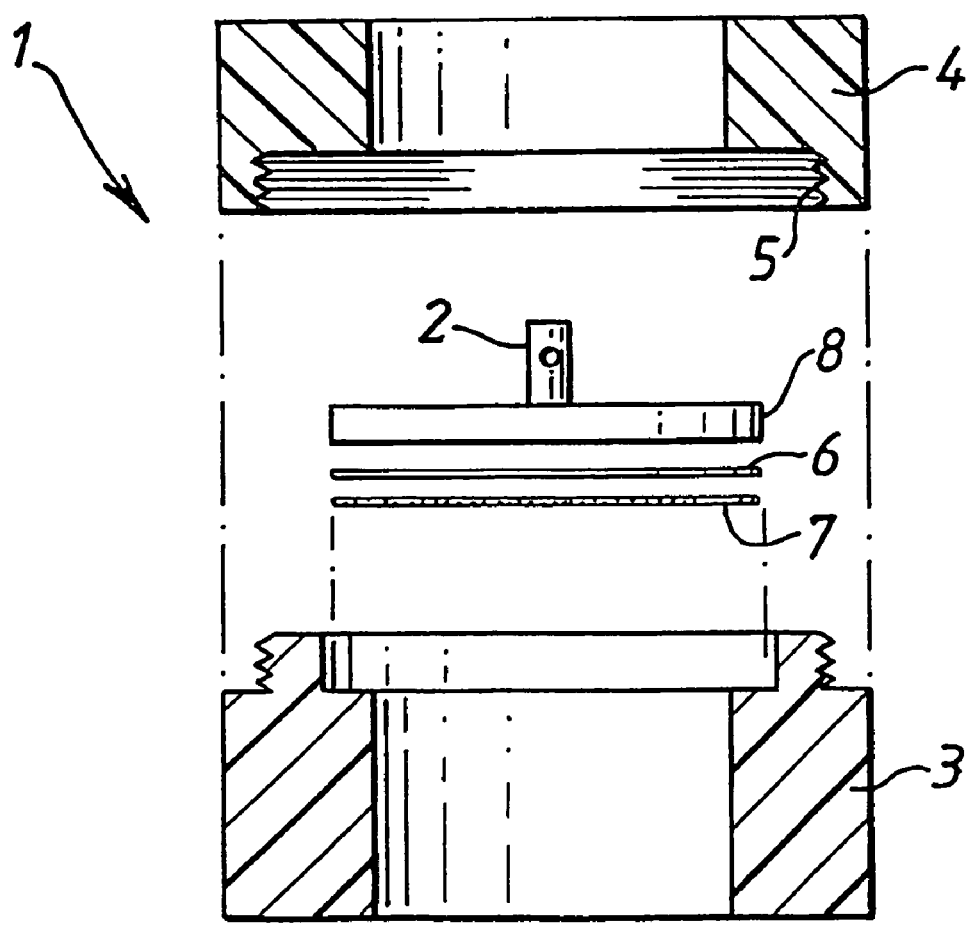
FIG. 1 is an exploded longitudinal section through a device for organic sampling according to the invention.

FIG. 1 shows a passive sampling unit comprising a substantially cylindrical PTFE body (1) having at its rear end one lug (2) adapted to provide fastening means for the unit in use, to prevent it from floating offsite. The body (1) is in two parts—a front part (3) and a rear part (4), which are water-tightly joinable by machined screw thread (5). When undone, the screw thread enables the unit to be taken apart to remove or insert the chromatographic receiving phase disk (6), which is positioned between the diffusion limiting membrane (7) to the front and a thin, rigid supporting PTFE disk (8) to the rear. In this example, the disk (8) has a diameter of 50 mm and is 5 mm thick. Any visible air bubbles are smoothed away from between the membrane (7) and receiving phase disk (6). On the opposite face, the supporting disc (8) has a machined round lug (e.g. 10 mm long and 5 mm in diameter) of PTFE with a small aperture (e.g. 3 mm in diameter) through which the device can be suspended during laboratory tank studies or field sampling (e.g. by wire or nylon cord (not shown)). The loaded supporting disc (8) (with receiving phase (6) and diffusion limiting membrane (7)) may be manually inserted into a locating ring in the front part (3) of the PTFE body (1). Holding the supporting disc (8) in position, the rear part (4) of the PTFE body (1) may be screwed into the front part of the body (1) to form a watertight seal between the outer face of the diffusion limiting membrane and the front segment of the body (1). Thus, the membrane (7) and supporting disk (8) are held in place between the two halves of the body (1). The front face (3) of the body (1) is open to allow contact between the aqueous environment (and the micropollutants therein) (not shown) and the membrane (7).

Figure 2:
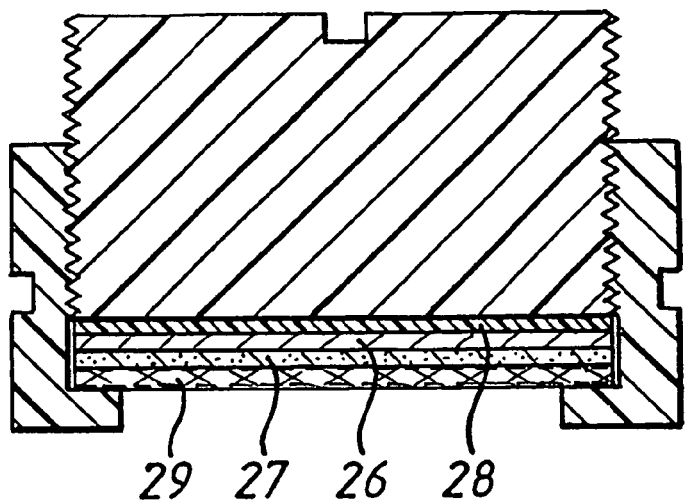
FIGS. 2 and 3 show cross-sectional and perspective views, respectively, of a device for inorganic sampling according to the invention.
Figure 3:
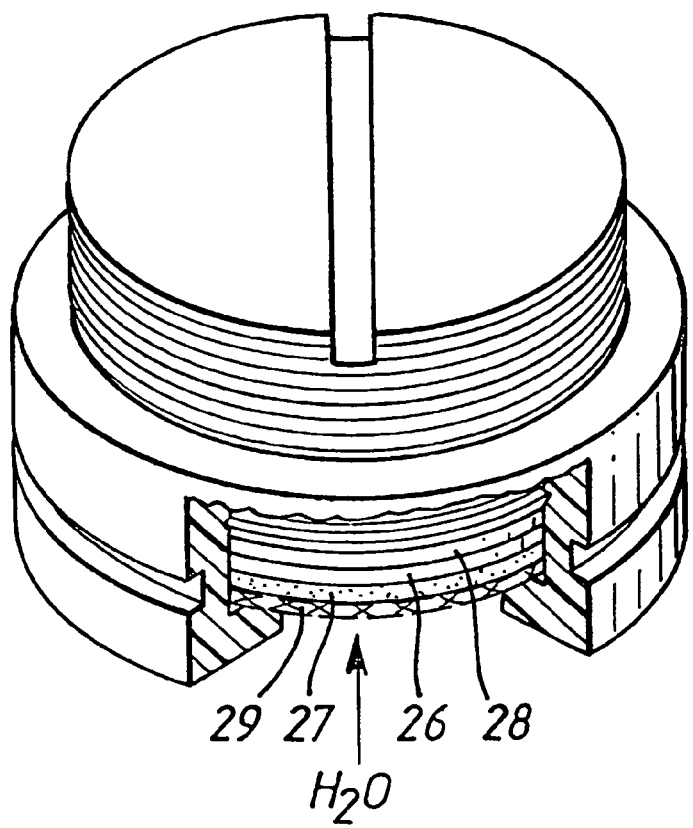

A similar embodiment is shown in FIGS. 2 and 3, but wherein the diffusion-limiting membrane (27) is protected by a 500 mm polypropylene net (29) on its face remote from the receiving phase (26). In this embodiment, the receiving phase (26) itself comprises a 3M Empore™ Extraction Disk; the diffusion-limiting membrane (27) is a Nafion™ 117-coated cellulose acetate membrane; and the supporting disk (28) is made of polypropylene.

Figure 4:
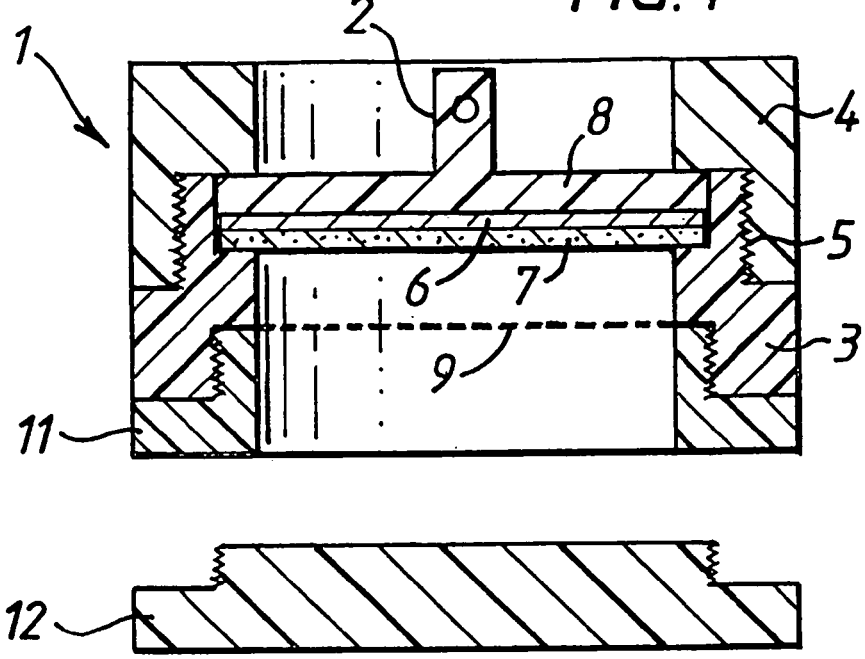
FIGS. 4 and 5 show cross-sectional and perspective views, respectively, of a device having a protective mesh and sealing plate according to the invention.
Figure 5:
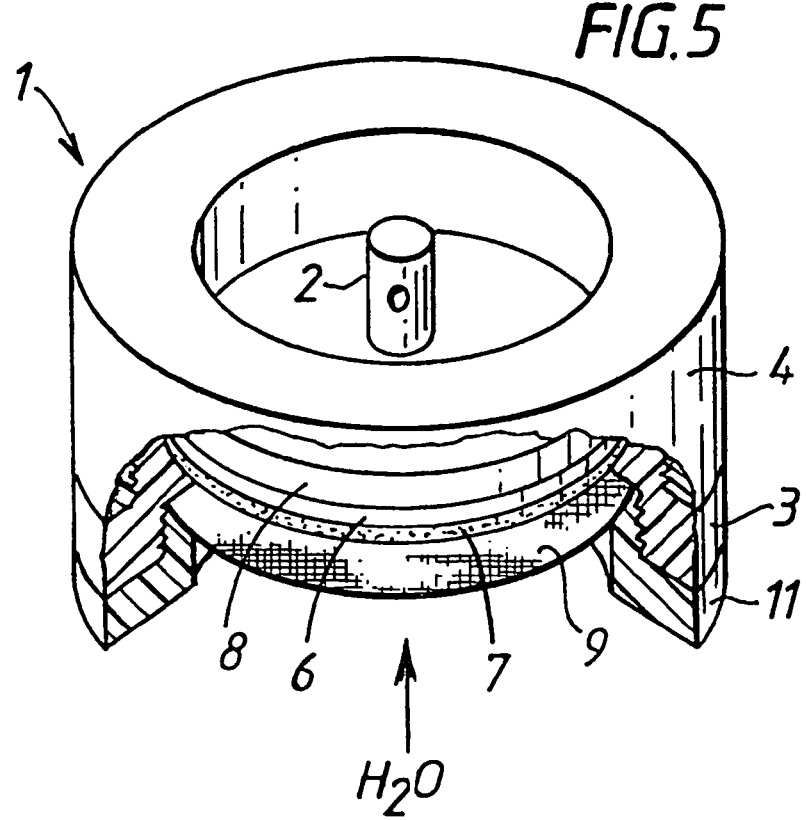

Likewise, FIGS. 4 and 5 show a similar embodiment to that of FIG. 1, but wherein the diffusion-limiting membrane (7) is protected by a stainless steel mesh (9), and the unit body (1) is further provided with a screw-threaded ring (11) for securing a sealing plate (12) for fitting into the base of the unit when not in use in the field.

In order that time-averaged aqueous concentrations can be calculated from accumulation of analytes in a passive sampling system, it is necessary that the rate of accumulation of compounds in the device is known. Furthermore, the effects on this calibration of fluctuating environmental conditions during the field deployment should be accounted for.

For this reason, extensive calibrations of the passive sampling units of FIGS. 1 to 3 (hereinafter sometimes referred to as "the prototype") have been carried out in a controlled laboratory environment. The effects of analyte concentration, water turbulence, temperature and device orientation on the uptake rates of the different prototypes have been assessed and the results obtained are described in Examples 3 to 6, respectively for the organic prototype, and the effects of time and concentration for the inorganic/chelating prototype in Example 7.

Analysis of Organic Micropollutants—Techniques

Organic Determinands—Test Micropollutants

In order to evaluate the prototype passive sampling system, the behaviour of a test set of six compounds: diuron, atrazine, phenanthrene, PCB 52, dieldrin and PCB 153 was chosen for study. The structures of these compounds are shown below. These compounds were chosen as they are known organic micropollutants commonly found in the aquatic environment and have a wide range of physico-chemical properties (see table 2).

TABLE 2

Some physico-chemical properties of the test set of organic compounds included for initial assessment as to their behaviour in the prototype passive sampling systems.

| Compound | Molecular mass | Log $K_{ow}$ | Solubility in water |
| --- | --- | --- | --- |
| Diuron | 233 | 2.68 | 42 mgl$^{-1}$ at 25° C. |
| Atrazine | 216 | 2.50 | 30 mgl$^{-1}$ at 20° C. |
| Phenanthrene | 178 | 4.46 | 1.3 mgl$^{-1}$ at 20° C. |
| PCB 52 | 292 | 6.10 | 0.03 mgl$^{-1}$ |

TABLE 2-continued

Some physico-chemical properties of the test set of organic compounds included for initial assessment as to their behaviour in the prototype passive sampling systems.

| Compound | Molecular mass | Log $K_{ow}$ | Solubility in water |
| --- | --- | --- | --- |
| Dieldrin | 381 | 4.58 | 0.186 mgl$^{-1}$ at 25° C. |
| PCB 153 | 361 | 6.90 | 0.00105 mgl$^{-1}$ |

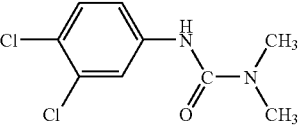

Diuron

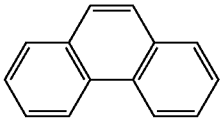

Phenanthrene

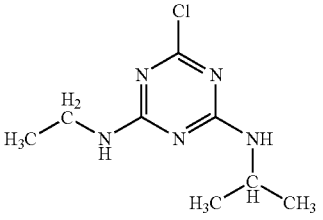

Atrazine

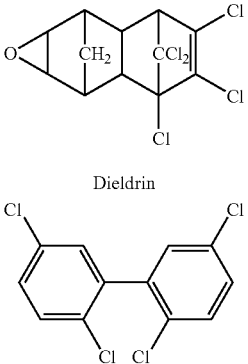

Dieldrin

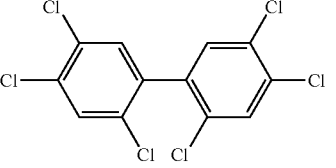

PCB 52

PCB 153

Techniques have been established for the quantitative isolation of the test set of six compounds both from aqueous and solid-phase media, and their subsequent determination using gas chromatography with mass selective detection.

Quantitative Analysis of Organic Micropollutants by Gas Chromatography with Mass Selective Detection (GC-MSD).

The six test compounds were simultaneously determined using gas chromatography with mass selective detection. The deuterated internal standard $^{10}$D-phenanthrene was used to correct for volumetric inaccuracies during sample preparation.

Materials:

Certified pure reference standards of each organic analyte were purchased from Qm$_x$ Saffron Walden, UK, (purity>98% in all cases). Individual stocks were produced at 1 mg/ml in HPLC grade acetone. Mixed calibration standards were prepared by suitable dilution of these stock solutions into HPLC grade 2,2,4-trimethylpentane. The gas chromatograph conditions and selective ion monitoring conditions (see table 3) are listed below.

TABLE 3

Selective ion monitoring conditions used for the determination of the test set of organic determinands by GC-MSD.

| Compound | Retention Time | Target | Qualifie |
|---|---|---|---|
| $^{10}$D-Phenanthrene | 9.54 | 188 | 80 |
| Diuron | 6.25 | 187 | 124 |
| Atrazine | 9.31 | 200 | 215 |
| Phenanthrene | 9.57 | 178 | 176 |
| PCB 52 | 10.38 | 292 | 220 |
| Dieldrin | 11.56 | 263 | 79 |
| PCB 153 | 12.04 | 360 | 290 |

Calibration Range: 0–2000 ng/ml
Instrument Conditions:

| | |
|---|---|
| Instrument: | Hewlett Packard 5890 GC with autosampler and mass selective detector |
| Mode: | Selective Ion Monitoring (SIM) |
| Column: | HP-5 (Crosslinked 5% phenyl methyl silicone) 30 m * 0.25 mm * 0.25 mm film thickness |
| Carrier gas: | Helium at 1 ml/min |
| Injection mode: | Pulsed splitless injection (2 min splitless) |
| Injection volume: | 2 ml |
| Injector temperature: | 275° C. |
| Detector Temperature: | 300° C. |
| GC oven temperatures: | Initial temperature 90° C. held for 3.0 minutes ramped at 20° C./min |
| Final temperature 280° C. held 3.0 mins | |

Extraction and Pre-Concentration of the Test Set of Organic Compounds from an Aqueous Matrix The six test compounds were extracted from aqueous solution by means of liquid—liquid extraction using two 10 ml aliquots of HPLC grade dichloromethane. 100 ml of a 1 ng/ml solution of $^{10}$D-phenanthrene in HPLC grade 2,2,4-trimethylpentane was added to the extract as an internal standard. The solvent was exchanged for 2,2,4-trimethylpentane and the sample concentrated under a stream of nitrogen to a volume of exactly 1.0 ml. The final extract was transferred to a 2 ml autosampler vial in preparation for analysis of pollutant levels by gas chromatography with mass selective detection (GC-MSD; see above).

Procedural Blanks and Recovery Standards

With each batch of samples extracted, a procedural blank consisting of a 100 ml aliquot of ultrapure water and two recovery solutions consisting of 100 ml ultrapure water spiked with 100 ng of each organic compound to be analysed were extracted. The recovery standards were analysed alongside unextracted calibration standards and a mean percentage recovery for the two extracts was calculated. This recovery factor was applied to the results of the samples in the same batch.

Thus sample results were produced, which were compensated for less than 100% extraction efficiency and batch to batch variations in method performance. Procedural blanks were again analysed alongside unextracted calibration standards to check for analytical interferences entering the system during the extraction procedure.

Typical percentage recoveries for each of the compounds contained in the test set are shown in table 4.

TABLE 4

Method performance of each organic analyte in the test set extracted from aqueous media and analysed using GC-MSD.

| Compound | Mean % recovery | % STD | Number of |
|---|---|---|---|
| Diuron | 104.2 | 5.6 | 10 |
| Atrazine | 106.7 | 4.0 | 10 |
| Phenanthr | 99.2 | 3.4 | 10 |
| PCB 52 | 98.0 | 4.1 | 10 |
| Dieldrin | 99.7 | 5.6 | 10 |
| PCB 153 | 92.5 | 5.9 | 10 |

Method of Organic Continuous-Flow Studies

An apparatus was devised which allows the constant mixing of organic analytes with water in an exposure tank.

This comprises a flow-through system for carrying out laboratory evaluations of the prototype device under controlled conditions. Ultrapure water is pumped and, separately, organic determinands dissolved in methanol are injected by syringe into the exposure tank at known and controlled rates. The tank has a fixed volume and an overflow to waste. This allows for the solution contained within the exposure tank to have a controlled (fixed or fluctuating) concentration of organic analytes for the long periods of time required for the laboratory calibrations of the prototype device. Furthermore, the tank can be stirred at a known rate using an overhead glass stirrer and the whole apparatus is situated in a controlled temperature environment.

Therefore, the rates of diffusion of all the test compounds through the chosen membrane materials and into the chosen receiving phase could be ascertained in a controlled laboratory environment.

Calibration of the Prototype Device with Different Diffusion-Limiting Membrane Materials.

The diffusion rates of the test set of organic determinands through differing membrane materials were tested by installing each membrane as the diffusion limiting membrane in the prototype device, and exposing the device to a solution of pesticides in the exposure tank of the flow-through system. In each experiment, a $C_{18}$ Empore™ disk (available from 3M) was used as the chromatographic receiving phase and the whole prototype device was exposed to an aqueous solution of organic analytes at known concentration for a fixed period of 48 h. During this experiment, the stirring speed was set at 140 rpm; the temperature of the system was kept constant at 11° C.; and dissolved analyte concentration was controlled and constant. 100 ml aliquots were taken from the exposure tank daily and the concentration of each analyte in the exposure tank was plotted on a daily basis. The prototype device was removed from the exposure tank following the 48 h exposure period and the mass of each analyte accumulated in both the $C_{18}$ Empore™ disk and the chosen membrane material was determined. This experiment was carried out in triplicate for each membrane material.

48 h accumulation factors ($AF_{48}$) were calculated for both the receiving phase and each diffusion-limiting membrane material. This accumulation factor gives a measurement of the uptake rate of the device fitted with different diffusion-limiting membranes related to the concentration of each analyte to which it is exposed and was calculated as follows:

$$48 \text{ h accumulation factor } (AF_{48}) = M_d/C_w$$

where: $M_d$=Mass in units of ng accumulated in the $C_{18}$ receiving phase following exposure for 48 h.

$C_w$=Average concentration in units of ng ml$^{-1}$ in the exposure tank during deployment.

Materials and Methods Used in Inorganic Tests $C_{18}$ Disks and Cartridges

The $C_{18}$ cartridge was Varian Bond Elut and the $C_{18}$ disks were 3M Empore™ (PTFE-support) and Supelco Envi-disk (glass fibre-support). Before separation, all cartridges and disks were conditioned with methanol (5 ml) and washed with ultrapure water (2×5 ml). Cartridges were held in a Varian vacuum assembly and disks were held in a Millipore filtration assembly.

Equilibration involved addition of hydroxylamine hydrochloride (reducing agent), sodium citrate (buffer adjusted to pH 4.3) and bathocuproine (2,9-dimethyl-4,7-diphenyl-1,10-phenanthroline-disulphonic acid, as photometric reagent) to an unfiltered sample. The final concentrations were: hydroxylamine hydrochloride, 0.12 M; sodium citrate, 0.01 M; bathocuproine, 0.036 M. Unless stated otherwise, all water samples contained 5% methanol to prevent loss of cartridge or disk conditioning. Bathocuproine was immobilised on the cartridge or disk by passage of 0.36 M bathocuproine in citrate buffer. Reducing agent, citrate buffer and methanol were added to the sample before passage over the immobilised bathocuproine. Total metal concentration was determined after ultraviolet irradiation of sample (100 ml), in the presence of 30% hydrogen peroxide (500 ml) and concentrated nitric acid (100 ml Scanpure), in a Metrohm UV-digester.

The Cu(I)-bathocuproine complex was eluted with methanol:water (90:10, vol:vol) from the cartridge (3×2 ml) or disk (3×5 ml). For each elution, the eluate was allowed to soak by drawing through one drop, standing for two minutes and then filtering through the rest of the eluate. Solutions were made up to volume with methanol:water (90:10, vol:vol) for cartridge (10 ml) or disk (25 ml). Absorbance (484 nm) was measured in a 1 cm cell in a Philips PU8620 spectrophotometer. The detection limit could be improved by the use of a longer cell. Each analysis was accompanied by a sample blank without added bathocuproine reagent. The blank was unreacted reagent and humic substances and was subtracted from the final result. The bathocuproine method for the determination of Cu (I) is described in more detail elsewhere (Moffett, et al., Analytica Chimica Acta 175, 171 (1985)). A linear calibration curve was found for 0–50 mgl$^{-1}$ Cu. Higher concentrations were not tested. All results for Cu determinations reported were carried out in at least duplicate and were within a relative standard deviation of ±1%.

Chelating Disk

The chelating resin disk (3M Empore™ Extraction Disk) was conditioned with ultrapure water (20 ml), 3M HNO$_3$, ultrapure water (2×40 ml), 0.1 M ammonium acetate pH 5.3 (50 ml) (Riedel-de Haen) and ultrapure water (2×40 ml). The chelating disk then contained iminoacetate groups in the matrix of inert PTFE, which collects multivalent metal ions by forming a complex similar to EDTA.

After the sampling period, the metals collected in situ on the exposed chelating disk in the passive sampler were either eluted with 3M HNO$_3$ (3×8 ml) and analysed with an Inductively Coupled Plasma-Mass Spectrometry (ICP-MS) to get the metal concentration, or the disk was analysed directly without elution, by direct laser ablation ICP-MS (LA-ICP-MS). Samples as 0.24 M HNO$_3$ were analysed for Cu, Zn, Cd and Pb by (ICP-MS) with correction for molecular ion interferences. The instrument used was a Perkin Elmer Elan 6000 and the laser ablation system coupled was a CETAC LSX 200.

Net

The net was made from polypropylene (500 mm, available from Industri Textil Job AB), and was acid washed (10% HNO$_3$) and rinsed with ultrapure water before use.

Prototype Passive Sampler

The passive sampler (FIGS. 2 and 3) was made of polypropylene, and was acid washed (10% HNO$_3$) and rinsed before use. After conditioning, the receiving disk (e.g. chelating disk, $C_{18}$) was placed in the passive sampler together with the diffusion limiting membrane and the protective net. The polypropylene holder was finally screwed together to make a water-tight seal. After exposure, the sampler was unscrewed, and the membranes were taken out and analysed.

Biofouling-Nafion Coating (Charge Exclusion-Negative Charge)

The diffusion-limiting membrane was treated with a Nafion coating (0.05% w/v, Nafion™117, Aldrich (Poole, UK) in an ethanol solution 1 ml). Periphyton experiments were done in a small creek Hultabäcken outside Göteborg. Periphyton is the term often used for the kind of microbial community that develops on an artificial substratum such as glass disks. The colonisation of a clean glass surface was initiated by bacteria. Periphyton were established on round, 14 mm diameter glass discs by using the periphyton sampling method of Blanck et al, in ASTM STP 988 American Society for Testing and Materials, Philadelphia, 219–230 (1998). The glass disks were held vertically by polyethylene holders attached to a polyethylene frame. The frame was attached to the bottom of the sampled stream by a polyethylene pole and left in situ for 2 to 3 weeks. The disks were impregnated with different amounts of Nafion to find out if Nafion could hinder biological growth. Growth was found to be slower with Nafion. The disks were analysed for chlorophyll a, the indicator of algal biomass. Five periphyton glass disks were handled together. They were cleaned on all sides, but the rough surface side, put into 1 ml of DMSO (dimethyl sulphoxide) and stored frozen until analysed. All handling and analysis were done in dim light. Then the chlorophyll a was extracted at 60° C. over 30 min. Once the samples had cooled down, an equal amount of acetone was added and the sample was centrifuged. The sample was then analysed spectrophotometrically. The chlorophyll a concentration was calculated according to the equation given by Jeffrey and Humphrey, Biochem. Physiol. Pflanzen. 167, 191–194 (1975).

LA-ICP-MS

Figure 6:
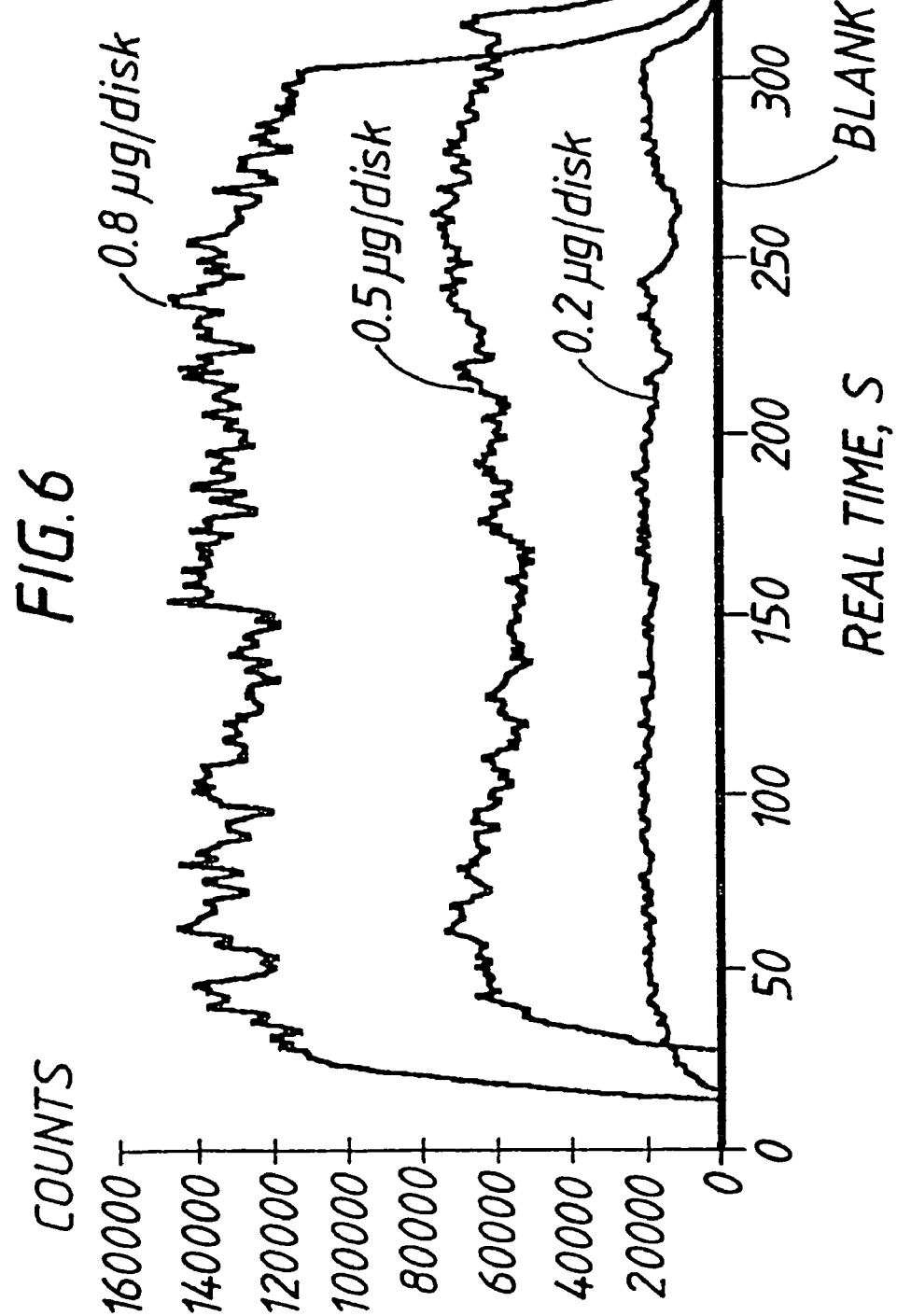
FIG. 6 shows direct Cu calibration of chelating disks useful for the receiving phase in devices according to the present invention by rastering the surface with an ultraviolet laser and direct injection of the Ar flow into the ICP-MS.

Laser ablation studies were done on chelating disks prepared with different metal concentrations in the laboratory and on disks from passive samplers that had been out in the field. A laser ablation system was coupled to the ICP-MS for the laser ablation studies and used to analyse chelating disks directly (see FIG. 6, which shows direct Cu calibration of chelating disks by rastering the surface with an ultraviolet laser and direct injection of the Ar flow into the ICP-MS. The average intensity (counts), used for calibration, is obtained from the plateaux. In this case, the elution step of the disk was excluded and a raster, series of three lines ('rastering'), was run on the surface, although it is also possible to go deeper in the matrix.

Laser ablation furthers the in situ advantages of passive sampling by direct analysis of the sampling chelating surface without sample preparation. It thereby avoids the contamination and sample alteration risks encountered during filtration and preparation of bottle samples.

Preparation and use of the passive sampler and method according to this invention will now be illustrated by the following examples.

EXAMPLE 1

Use of Prototype Passive Sampling Device Having $C_{18}$ Disks

Preparation of $C_{18}$ Empore™ Disks $C_{18}$ Empore™ disks required conditioning prior to their use as receiving phase for the passive sampling system. The conditioning process consisted of soaking the disks in HPLC grade methanol (10 ml, from Fischer Scientific) for 20 minutes in a glass beaker. During this time the disk took on a translucent appearance. The disks were then transferred to a glass beaker or petri dish containing ultrapure water to remove excess methanol. The disk was removed for the water and pressed gently with a clean, dry tissue to remove excess water.

Disks of membrane material were prepared with a diameter of 47 mm. The conditioned $C_{18}$ disks were laid directly onto the PTFE loading or support disk.

The diffusion-limiting membrane was placed over the $C_{18}$ disk and any visible air bubbles were smoothed away from between the two membranes. The loading disk (complete with chromatographic phase and diffusion-limiting membrane) was then placed into the device body (FIG. 1) and screwed in place to form a watertight seal.

Storage and Deployment of the Passive Sampling Device

The $C_{18}$ disks were not allowed to dry out between conditioning and deployment of the device. Therefore, either the devices were loaded immediately before deployment or the loaded devices were stored immersed in ultrapure water in a sealed vessel, such as a glass jar, prior to deployment. They should be transported stored in this way to the deployment site and removed only immediately prior to use. Alternatively, the passive sampler can be filled with distilled water and sealed using a sealing plate, as in the case of the sampler shown in FIGS. 4 and 5, component (12) until deployment. The device was removed from the storage jar and a support wire or cord was fastened to the lug on the PTFE support disc. The wire or cord was of sufficient length to allow the device, once deployed, to be suspended totally submerged beneath the water surface throughout the sampling period. In the field, the wire or cord may be secured to a buoy or similar structure. The device was lowered into the water and any air trapped in the front face of the sampler body was removed by briefly inverting the assembly. The device was then allowed to hang freely in the water. The device naturally hangs with the exposed face of the diffusion limiting membrane pointing downwards.

Retrieval

After the required deployment period, the device was taken from the sampling site and disassembled. Disassembly followed the reverse of that described above for assembly. The chromatographic receiving phase was removed, such as by using clean stainless steel forceps, and was placed in a clean glass screw top vial fitted with a PTFE-lined cap. The chromatographic phase was stored at $-20°$ C. prior to analysis. The diffusion limiting membrane was discarded. The PTFE body and supporting disc were washed with water and organic solvents prior to re-use.

Extraction of the Test Set of Organic Compounds from $C_{18}$ Empore Disks

The organic determinands were extracted from the $C_{18}$ Empore™ disks using 5 ml of HPLC grade acetone (for 5 min in an ultrasonic bath) followed by 10 ml of 50%:50% (vol/vol) ethylacetate:2,2,4-trimethylpentane mixture (for 5 min in an ultrasonic bath). At the end of this time, the disk was removed, the two solvent extracts were combined and 100 ml of the 1 ng/ml solution of deuterated $^{10}$D-phenanthrene added as an internal standard. The extract was concentrated to a volume of 1 ml under a stream of nitrogen and the extract was placed into 2 ml auto-sampler vials in preparation for determination by GC-MSD.

EXAMPLE 2

Evaluation of Membrane Materials Suitable for Use in the Prototype

The diffusional properties of some commercially available membrane materials (see Table 1) were assessed by exposure of the prototype sampler of Example 1 in the continuous-flow system as described above. The accumulation of organic analytes in the $C_1$ receiving phase following 48 h exposure of the prototype device fitted with each membrane material is summarised in Table 5. The experiment was carried out at constant analyte concentration, at a temperature of 11° C. and at a constant stirring speed of 140 rpm. Error bars show standard deviations (n=3). Results are quoted as an accumulation factor (ml/device)=concentration in the receiving phase (ng/device)/mean concentration of the analyte in the aqueous phase during deployment (ng/ml). Numbers in parentheses show standard deviations (n=3).

TABLE 5

|  | Diuron | Atrazine | Phenanthrene | PCB 52 | Dieldrin | PCB 153 |
| --- | --- | --- | --- | --- | --- | --- |
| No membrane | 844 (268) | 962 (59) | 1164 (128) | 1118 (115) | 1094 (42) | 1048 (145) |
| 0.2 μm pore size polysulphone membrane | 140 (12) | 168 (17) | 0 (0) | 0 (0) | 0 (0) | 0 (0) |
| 1.0 μm pore size PTFE membrane | 84 (4) | 98 (3) | 101 (7) | 16 (9) | 52 (5) | 53 (24) |
| 0.2 μm pore size polycarbonate membrane | 150 (8) | 148 (8) | 11.7 (5) | 7.1 (6) | 13 (14) | 5 (38) |

TABLE 5-continued

|  | Diuron | Atrazine | Phenanthrene | PCB 52 | Dieldrin | PCB 153 |
|---|---|---|---|---|---|---|
| 0.2 μm pore size PVDF membrane | 115 (7) | 106 (9) | 22 (3) | 18 (8) | 19 (2) | 11 (3) |
| glass fibre | 51 (21) | 52 (20) | 118 (10) | 81 (6) | 67 (10) | 43 (8) |
| 1000 MWCO cellulose dialysis membrane | 150 (30) | 121 (16) | 143 (9) | 20 (13) | 94 (23) | 7 (29) |
| Polyethylene (type 1) | 0 (0) | 0 (0) | 1028 (125) | 740 (240) | 256 (55) | 233 (115) |
| Polyethylene (type 2) | 0 (0) | 0 (0) | 1048 (95) | 819 (81) | 114 (14) | 215 (40) |
| Polyethylene (type 3) | 0 (0) | 0 (0) | 643 (16) | 262 (15) | 1.0 (1) | 68 (11) |
| PVC | 0 (0) | 0 (0) | 276 (84) | 94 (30) | 19 (11) | 17 (6) |

The pattern of accumulation of compounds in the $C_{18}$ receiving phase is affected by the physico-chemical properties of both the membrane material and the target analyte. Some of the more non-polar compounds such as the PCBs, dieldrin and phenanthrene have a high affinity for a particular membrane material and therefore accumulate within the structure of this membrane and do not pass through into the receiving phase. In contrast, some of the polymeric membranes provided for rapid transport of non-polar analytes but formed a barrier for the transport of the more polar analytes such as diuron and atrazine.

The pattern of accumulation of organic analytes within the two compartments of the passive sampling system fitted with different membrane materials is illustrated in Table 6. The device is fitted with a $C_{18}$ Empore™ disk as the receiving phase and either a 0.2 mm pore size polysulphone membrane or a polyethylene membrane as the diffusion limiting membrane material. Accumulation was measured following a 48 hour exposure to aqueous solution of analytes at constant concentration, constant stirring speed (140 rpm) and constant temperature (11° C.). Results quoted are the average of three replicates and are expressed as an accumulation factor (ml/device)=mass in the tested compartment (ng/device)/mean concentration of the analyte in the aqueous phase during deployment (ng/ml); values in parentheses show standard deviations (n=3).

relatively polar compounds with log $K_{ow}$<4, such as atrazine and diuron. This material is therefore a suitable diffusion-limiting membrane for a passive sampling system targeting non-polar organic micropollutants.

The following section and Examples 3 to 5 describe the results obtained from laboratory exposures of the prototype device in controlled conditions in the flow-through system described above. Accumulation of analytes within the receiving phase of the passive sampling system following exposure was determined by means of solvent extraction and gas chromatographic analysis as described in the discussion of the analysis of organic micropollutants—techniques, above.

In each experiment, the prototype device was tested fitted with both the polyethylene and the polysulphone membrane. Therefore the results quoted for the non-polar analytes phenanthrene, dieldrin, PCB 52 and PCB 153 were produced using the system fitted with the polyethylene membrane and the results quoted for the more polar analytes diuron and atrazine were produced using the polysulphone system.

Calibration of the Prototype Passive Sampling Systems at Constant Exposure Concentration Over Time Table 7 shows the uptake pattern of organic analytes by the passive sampling device exposed in a controlled laboratory environment to a constant concentration of organic

TABLE 6

|  | Diuron | Atrazine | Phenanthrene | PCB 52 | Dieldrin | PCB 153 |
|---|---|---|---|---|---|---|
| $C_{18}$ Empore ™ disk with polysulphone membrane | 140 (12) | 168 (17) | 0 (0) | 0 (0) | 0 (0) | 0 (0) |
| Polysulphone membrane | 64 (21) | 9 (8) | 935 (188) | 875 (169) | 634 (107) | 498 (171) |
| $C_{18}$ Empore ™ disk with polyethylene membrane | 0 (0) | 0 (0) | 1028 (125) | 740 (240) | 256 (55) | 233 (115) |
| Polyethylene membrane | 0 (0) | 0 (0) | 48 (4) | 116 (47) | 143 (15) | 177 (141) |

In particular, can be noted:

The polysulphone membrane has a high degree of physical strength and is available in a low protein binding formula that may have antifouling properties. It has a high affinity for the more hydrophobic compounds included in this study i.e. phenanthrene, dieldrin and the PCBs, but the more polar compounds such as atrazine and diuron readily pass through this membrane material and are accumulated in the receiving phase of the passive sampling device. The polysulphone membrane is therefore suitable for use in a passive sampling system for the targeting of relatively polar micropollutants with typical log $K_{ow}$ values of less than 4.

The polyethylene membrane allows the rapid diffusion of non-polar analytes, but forms a barrier for the diffusion of analytes for a range of different exposure periods. Accumulation of organic analytes by a passive sampling system fitted with a $C_{18}$ Empore™ disk as receiving phase and either a 0.2 mm pore size polysulphone membrane or a polyethylene membrane as a diffusion-limiting membrane material. Accumulation was measured following exposure of the system to an aqueous solution of analytes at constant concentration, stirring speed (140 rpm) and temperature (11° C.). Linear regressions of the accumulation factor, AF, (ml/device) on time were plotted and are given with the coefficients of variation ($R^2$) in table 7. AF=mass of analytes in the tested compartment (ng/device)/mean concentration of the analyte in the aqueous phase during deployment (ng/ml).

TABLE 7

| Analyte | Linear regression | R² value |
|---|---|---|
| Diuron* | Y = 1.64x + 13.7 | 0.954 |
| Atrazine* | Y = 2.42x + 4.15 | 0.990 |
| Phenanthrene• | Y = 25.51x + 131.9 | 0.939 |
| PCB 52• | Y = 29.55x + 149.5 | 0.984 |
| Dieldrin• | Y = 9.16x − 100.6 | 0.973 |
| PCB 153• | Y = 13.40x − 182.8 | 0.909 |

*sampler fitted with polysulphone membrane,
•sampler fitted with polyethylene membrane The pattern of uptake in each case is linear with time over deployment periods ranging from several hours to 9 days. $R^2$ values in each case are above 0.9. Linear regressions plotted through the data points show the lag time between exposure of the device to an aqueous solution of each analyte and its uptake into the receiving phase of the passive sampling system. In effect this is a measurement of the response time of a particular prototype passive sampling system to a particular compound. In the case of the uptake of phenanthrene and PCB 52 into the polyethylene device, only a small lag phase is evident between exposure to these analytes dissolved in an aqueous environment and uptake into the $C_{18}$ receiving phase. In the case of the uptake of PCB 153 and dieldrin, on the other hand, a more significant lag phase is observed between exposure to dissolved compounds in aqueous solution and uptake into the passive sampler.

As each graph is essentially linear, the time-averaged concentration of each of the dissolved analytes in aqueous solution can be easily predicted from the final analyte mass in the receiving phase of the passive sampling system at the end of a deployment period.

EXAMPLE 3

Effect of Exposure Concentration on the Uptake of Organic Analytes

According to the principles of Fickian diffusion, the uptake of each organic analyte by the receiving phase of the passive sampling system should be linearly related to the analyte concentration in the surrounding water. The device with chosen diffusion-limiting membrane and $C_{18}$ Empore disk as receiving phase was placed into the exposure tank described above containing a known concentration of dissolved organic analytes at a temperature of 11° C. and with the exposure tank stirred at 140 rpm. The device was exposed to this fixed concentration for a period of 48 h following which it was removed and the mass of each analyte accumulated in the receiving phase of the device was measured (see Example 1, using GC-MSD). 100 ml samples were taken from the exposure tank daily and the concentration of each analyte in the exposure tank was plotted on a daily basis. This experiment was repeated at a range of dissolved analytes concentrations.

Table 8 shows accumulation of each organic compound in the receiving phase of the prototype passive sampling device following exposure to different analyte concentrations in the controlled flow-through system for 48 h period. Linear regressions were effected for the accumulation factor of each analyte, AF, (ml/device) on the mean water concentration during deployment (ng/ml) and the resulting equations are given with the coefficients of determination ($R^2$) in table 8. AF analyte mass in the tested compartment (ng/device)/ mean concentration of the analyte in the aqueous phase during deployment (ng/ml).

TABLE 8

| Analyte | Linear regression | R² value |
|---|---|---|
| Diuron* | Y = 0.0871x + 5.12 | 0.997 |
| Atrazine* | Y = 0.1231x + 5.95 | 0.994 |
| Phenanthrene• | Y = 1.126x + 28.7 | 0.974 |
| PCB 52• | Y = 1.024x − 4.01 | 0.951 |
| Dieldrin• | Y = 0.409x − 9.84 | 0.985 |
| PCB 153• | Y = 0.673x + 1.48 | 0.969 |

*sampler fitted with polysulphone membrane,
•sampler fitted with polyethylene membrane Again, the calibration graphs plotted are essentially linear, with $R^2$ values ranging from 0.9510 in the case of PCB 52 to 0.9969 in the case of diuron. This shows that the rate of uptake of each analyte into the passive sampling device is dependent on concentration in the aqueous environment. The mass of organic analytes accumulated in the receiving phase of the passive sampler following a known deployment period is therefore directly related to the concentration to which the device has been exposed.

EXAMPLE 4

Effect of Temperature on Uptake Rate of Organic Analytes

The prototype device was placed in the exposure tank described above calibrated at fixed analyte concentration and a stirring speed of 140 rpm for time periods ranging from one day to one week. The initial experiment was undertaken in a controlled temperature environment with a resultant water temperature of 11° C. At the end of each exposure the prototype device was removed and the mass of each analyte accumulated within the receiving phase was determined. The experiment was repeated in its entirety at temperatures of 4° C., 7° C. and 15° C. to assess the effect of temperature on uptake rates of organic analytes by the passive sampling system.

Table 9 shows the results; the natural logarithm of the slope was regressed upon the reciprocal of absolute temperature to yield the regression coefficients (slopes in table 9). These slopes have units of K and when multiplied by the universal gas constant ($JK^{-1}mol^{-1}$) give activation energies ($Jmol^{-1}$). The coefficients of determination ($R^2$) give a measure of the magnitude of the association of the natural log of the rate and 1/T in each case.

TABLE 9

| Analyte | Linear regression | R² value |
|---|---|---|
| Diuron* | Y = −5083x + 18.75 | 0.778 |
| Atrazine* | Y = −4464x + 16.67 | 0.938 |
| Phenanthrene• | Y = −3228x + 14.45 | 0.876 |
| PCB 52• | Y = −3099x + 14.06 | 0.717 |
| Dieldrin• | Y = −9153x + 34.19 | 0.940 |
| PCB 153• | Y = −3855x + 16.10 | 0.602 |

*sampler fitted with polysulphone membrane,
•sampler fitted with polyethylene membrane Alteration in exposure temperature produces an effect on the uptake pattern of organic analytes by the passive sampling system. This effect is largest in the case of the uptake of dieldrin by the device fitted with a polyethylene diffusion-limiting membrane.

EXAMPLE 5

Effect of Device Orientation on the Uptake Rates of Organic Analytes

The prototype device was calibrated by placing in the exposure tank of the flow-through system described above for a period of 48 h. The exposure concentration was kept constant, the temperature was set at 11° C. and the system was stirred at 140 rpm during this experiment. At the end of each exposure the prototype device was removed and the mass of each analyte accumulated within the receiving phase was determined. This experiment was carried out with five replicates with the diffusion limiting membrane in a vertical orientation and a horizontal orientation to investigate the effect of device orientation on the uptake rate of organic analytes by the passive sampling device.

48 hour exposure of the prototype passive sampling device with the membrane in a vertical orientation and horizontal orientation showed that the orientation of the device has no significant effect on uptake rates of the organic analytes by the passive sampling systems. This is the case with both the polysulphone device and the polyethylene device.

EXAMPLE 6

Laboratory Tests Using Chelating Prototype

Example 6 relates to a passive sampler (inorganic prototype, FIGS. 2 and 3) according to the invention comprising a 3M Empore™ Extraction Disk (chelating disk) as the receiving disk; a Nafion™ 117-coated cellulose acetate diffusion-limiting membrane and a 500 mm polypropylene net, in accordance with the description of materials and methods used in inorganic tests, above.

Experiments were done to calibrate the device. Time-exposed passive sampler experiments were done in a Cu and Zn concentration of 500 mg/l, in 300 ml $H_2O$ and during 1–5 hours with magnetic stirring. The passive samplers were taken out of the water hourly during 5 hours and were then analysed for Cu and Zn in a flame atomic absorption spectrometer, AAS (Perkin Elmer 2380). Calibration lines for Cu of y=78.182x+104.07, $R^2$=0.9796, for Zn of y=94.554x+99.655, $R^2$=0.9789, respectively, were found, where y is the concentration in mg/l and x is the time in hours.

Experiments were done in the same way for concentration-exposed passive samplers from 50–500 mg/l for Cu and Zn, in 300 ml $H_2O$ and during 5 hours with magnetic stirring. All the passive samplers were taken out of the water after 5 hours and analyzed. The calibration line for Cu was y=0.0427x+1.1333, $R^2$=0.9937, and for Zn was y=0.2117x+29.689, $R^2$=0.9864, where x is the concentration in mg/l and y is the absorbance in %.

EXAMPLE 7

Use of Prototype Passive Sampling Device Having Internal Standard

The method of Example 1 was followed, with the following adaptations: first, the conditioned $C_{18}$ disks were preloaded with an internal standard. The internal standard was introduced to compensate for alterations to analyte uptake by the passive sampler due to fluctuations in environmental conditions (eg temperature and turbulence) during deployment. The conditioned $C_{18}$ Empore™ disk was placed in a standard filtration apparatus. 100 ml of ultrapure water were spiked with 1000 μl of a solution of 100 ng/μl $D_8$-naphthalene and $D_6$-dimethylphthalate in methanol. The solution was filtered through the $C_{18}$ Empore™ disk under vacuum and the disk was immediately placed into the device with the diffusion-limiting membrane.

Secondly, the device was that of FIGS. 4 and 5. The device was placed face up, and a few milliliters of ultrapure water were placed in the upper cavity before the system was sealed for transportation and storage using the sealing plate.

During deployment, the sealing plate was removed from the device, and a stainless steel protective mesh was fitted in place and secured using the screw thread ring provided.

After the required deployment period, the device was taken from the sampling site and the inner cavity of the device was filled with a few milliliters of water from the sampling site. The sealing plate was screwed tightly onto the device to create a watertight seal. For field use, the device should be refrigerated (or preferably frozen at −20° C.) for transportation prior to analysis. The system was disassembled (reversing the procedure outlined above for assembly) immediately prior to analysis, as described in Example 1.

Following deployment, the mass of analyte accumulated within the passive sampler was found to be proportional to the mass of internal standard lost from the sampler for a range of temperatures and levels of water turbulence. Therefore, rate of accumulation of analyte could be adjusted for differing environmental conditions.

EXAMPLE 8

Permselective Membrane Diffusion in the Passive Sampler

The permselectivity of the Nafion™-coated cellulose acetate membrane has been tested in the laboratory for water samples (Table 10). The uncoated cellulose membrane in the passive sampler (ie comprising the same sampler as described in Example 6 but uncoated) shows comparable results with the electrochemical measurements for Cu and Zn, which confirms that the same diffusion mechanism is involved. For Cd, the colloidal associations fail to penetrate even an uncoated membrane.

The permselective mechanism is confirmed for the Nafion™-coated cellulose membrane for all metals (Table 10). For Cu, negatively charged organic complexes are effectively excluded which gives an availability for Cu of 1%. For cadmium, the organic complexes are excluded by both coated and uncoated membranes. Zinc shows an intermediate behaviour with further evidence of organic complex exclusion.

Table 10: Percentage availability of metals to the passive sampler for urban river water, under laboratory experimental conditions. The values are calculated from uptake of free ion for the same total concentration, so the values represent the relative availability of metals in the sample to the passive sampler. Electro-availability refers to the same fraction but in terms of availability at a naked mercury drop electrode.

| Cellulose membrane | Cadmium | Copper | Zinc |
| --- | --- | --- | --- |
| Nafion coated | 0.03 | 1 | 8 |
| Uncoated | 0.05 | 20 | 20 |
| Electroavailability | 17 | 12 | 21 |

Figure 7:
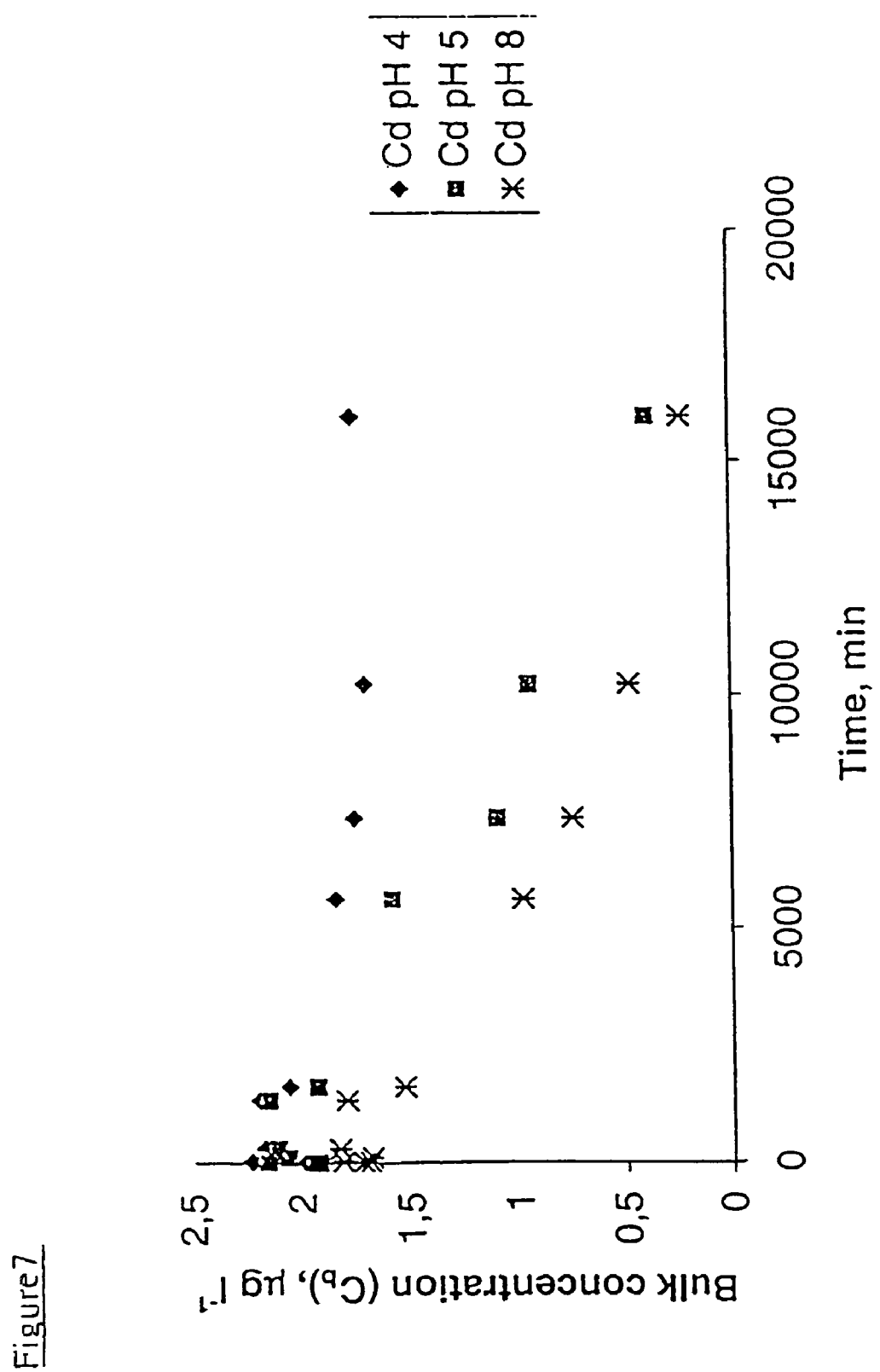
FIG. 7 shows the effect of varied pH (4, 5 and 8) for cadmium uptake by the passive sampling device of FIGS. 2 and 3 fitted with a Nafion™-coated cellulose acetate membrane.

Further evidence for the permselective function of the membrane during diffusion is illustrated by studying the effect of pH on metal uptake by the passive sampler, in this case Cd. FIG. 7 shows the effect of varied pH (4, 5 and 8) for cadmium uptake by the passive sampling system fitted with a Nafion™-coated cellulose acetate membrane. Cadmium was initially added to a carefully-controlled water system in the laboratory into which the sampler was placed. Samples of water were taken over a period of 10 days.

The significantly lowered uptake at pH 4 relates to a change in charge characteristics of the Nafion™ polymer coating and is direct evidence that transport through the permselective coating is through interaction with Nafion™. Further evidence of the interaction of metal with the permselective membrane is that uptake to a naked disk is much more rapid. The uptake rate constant (k) for Cd is $1.6 \times 10^9$ $min^{-1}$ for the naked disk and $0.21 \times 10^9$ $min^{-1}$ for the permselective membrane.

The invention claimed is:

1. A passive sampling device for accumulating over a period of time micropollutants from an aquatic environment, which device comprises:
   (a) a diffusion-limiting membrane contactable in use with the aquatic environment and adapted to allow rate-limited diffusion therethrough of the micropollutants; and
   (b) a receiving phase having a sufficiently high affinity for the micropollutants for accumulating the micropollutants;
   wherein the receiving phase is:
   (i) a removable unitary element;
   (ii) separated from the aquatic environment by said membrane;
   (iii) comprised of a solid phase material immobilised by being bound in or to a hydrophobic solid support, the solid support comprising a matrix of fibres.

2. A device according to claim 1, wherein the solid support is in the form of a solid carrier for the solid phase material, which does not contain or retain water within its structure and can not exchange water with its environment, whereby the solid support is not subject to loss of water and hence changes in dimension, due either to evaporation or osmotic efflux.

3. A device according to claim 1, wherein the diffusion-limiting membrane comprises a solid, hydrophobic material, which contains less than 1% water and/or is substantially non-porous, whereby the diffusion pathway comprises the solid polymer itself and not any water contained therein.

4. A device according to claim 1, wherein the diffusion-limiting membrane comprises polyethylene.

5. A device according to claim 1, suitable for accumulating polar, organic micropollutants wherein the membrane is selected from polysulphone, polycarbonate, cellulose dialysis membrane, PTFE, PVDF and glass fibre.

6. A device according to claim 1, suitable for accumulating inorganic micropollutants, wherein the membrane is selected from cellulose acetate, glass fibre membranes, nylon membranes and dialysis membranes.

7. A device according to claim 1, wherein the diffusion-limiting membrane is or is associated with a molecular charge selective material.

8. A device according to claim 7, wherein the molecular charge selective material is selected from poly(4-vinylpyridine), poly(2,6-dimethylphenol) and perfluorinated polymers having pendant sulphonic acid groups.

9. A device according to claim 1, wherein the thickness of the membrane, and therefore diffusion pathway, is in the range of from 0.02 to 0.15 mm.

10. A device according to claim 9, wherein the thickness of the membrane, and therefore diffusion pathway, is less than 0.1 mm.

11. A device according to claim 1, wherein the thickness of the receiving phase is less than 1 mm.

12. A device according to claim 1, wherein the solid receiving phase is in the form of a cartridge or disk.

13. A device according to claim 1, wherein the immobilized solid phase material comprises $C_8$ to $C_{18}$ chain length hydrocarbon groups bonded in a silica-based polymer.

14. A device according to claim 1, wherein the matrix of fibres comprises hydrophobic fibres.

15. A device according to claim 1, wherein a face of the membrane remote from the receiving phase is provided with netting or a mesh.

16. A device according to claim 1, further comprising an inert housing in which said receiving phase and said diffusion limiting membrane are removably mountable, said housing being adapted to allow access of micropollutants to the receiving phase through the diffusion limiting membrane.

17. A device according to claim 16, further comprising removable means for enabling water or conditioning liquid to be maintained in contact with the solid receiving phase between preparation and use of the device.

18. A device according to claim 17, wherein the housing and/or removable means comprises PTFE.

19. A passive sampling method for monitoring over a period of time the concentrations of micropollutants in a polluted environment, which method comprises:
   (a) providing a receiving phase having a sufficiently high affinity for the micropollutants for accumulating the micropollutants, the receiving phase being a unitary element comprising a solid phase material immobilised by being bound in or to a hydrophobic solid support, the solid support comprising a matrix of fibres;
   (b) providing a diffusion-limiting membrane adapted to allow rate-limited diffusion therethrough of the micropollutants;
   (c) separating said receiving phase from said polluted environment using said membrane;
   (d) bringing the membrane into contact with said polluted environment for a sufficient period of time to allow the micropollutants to accumulate in said receiving phase;
   (e) removing said receiving phase from said polluted environment; and
   (f) analysing the micropollutants accumulated in said receiving phase.

20. A method according to claim 19, wherein, in step (e), the solid receiving phase is removed from the environment and separated from the membrane.

21. A method according to claim 19, wherein the step (f) comprises applying extraction solvent to the receiving phase, whereby the micropollutants are removed from the receiving phase.

22. A method according to claim 21, wherein the extraction solvent is applied to one face of the receiving phase and is collected, containing the micropollutants, at the opposite face thereof.

23. A method according to claim 19, which further comprises pre-treating the receiving phase by coating it with diffusion-limiting membrane; by conditioning it with a conditioner; or by loading it with internal standard; or any combination thereof.

24. A method according to claim 19, which further comprises pre-treating the receiving phase by treating it with an agent adapted to complex, chelate or otherwise assist the receiving phase to accumulate the chosen micropollutant.

25. A method according to claim 19, which further comprises pre-treating the receiving phase by coating or impregnating it with a photometric agent selected from bathocuproine, methylthymol blue, xylenol orange, glycine cresol red, binchinonic acid and 1,5-diphenyl carbohydrazide.

26. A method according to claim 19, which further comprises pre-treating the receiving phase by coating or impregnating it with an internal standard comprising an istopically-labelled compound, capable of, during deployment of the device, diffusing from the receiving phase through the diffusion-limiting membrane and into the aquatic environment at a known and controlled rate.

27. A passive sampling device for accumulating over a period of time non-polar, organic micropollutants from an aquatic environment, which device comprises:
(a) a diffusion-limiting membrane contractable in use with the aquatic environment and adapted to allow rate-limited diffusion therethrough of the micropollutants; and
(b) a receiving phase having a sufficiently high affinity for the micropollutants for accumulating the micropollutants;
wherein the receiving phase is:
(i) a removable unitary element;
(ii) separated form the aquatic environment by said membrane;
(iii) comprised of a solid phase material immobilised by being bound in or to a hydrophobic solid support, the solid support comprising a matrix of fibres,
and wherein the diffusion-limiting membrane comprises a solid, hydrophobic polymeric material capable of determining the rate of diffusion of the micropollutants therethrough.

28. A device according to claim 27, wherein the solid support is in the form of a solid carrier for the solid phase material, which does not contain or retain water within its structure and can not exchange water with its environment, whereby the solid support is not subject to loss of water and hence changes in dimension, due either to evaporation or osmotic efflux.

29. A device according to claim 27, wherein the diffusion-limiting membrane comprises a solid, hydrophobic material, which contains less than 1% water and/or is substantially non-porous, whereby the diffusion pathway comprises the solid polymer itself and not any water contained therein.

30. A device according to claim 27, wherein the diffusion-limiting membrane comprises polyethylene.

31. A device according to claim 27, suitable for accumulating polar, organic micropollutants, wherein the membrane is selected from polysulphone, polycarbonate, cellulose dialysis membrane, PTFE, PVDF and glass fibre.

32. A device according to claim 27, suitable for accumulating inorganic micropollutants, wherein the membrane is selected from cellulose acetate, glass fibre membranes, nylon membranes and dialysis membranes.

33. A device according to claim 27, wherein the diffusion-limiting membrane is or is associated with a molecular charge selective material.

34. A device according to claim 33, wherein the molecular charge selective material is selected from poly(4-vinylpyridine), ply(2,6-dimethylphenol) and perfluorinated polymers having pendant sulphonic acid groups.

35. A device according to claim 27, wherein the thickness of the membrane, and therefore diffusion pathway, is in the range of from 0.02 to 0.15 mm.

36. A device according to claim 35, wherein the thickness of the membrane, and therefore diffusion pathway, is less than 0.1 mm.

37. A device according to claim 27, wherein the thickness of the receiving phase is less than 1 mm.

38. A device according to claim 27, wherein the solid receiving phase is in the form of a cartridge or disk.

39. A device according to claim 27, wherein the immobilised solid phase material comprises $C_8$ to $C_{18}$ chain length hydrocarbon groups bonded in a silica-based polymer.

40. A device according to claim 27, wherein the matrix of fibres comprises hydrophobic fibres.

41. A device according to claim 27, wherein a face of the membrane remote from the receiving phase is provided with netting or a mesh.

42. A device according to claim 27, further comprising an inert housing in which said receiving phase and said diffusion limiting membrane are removably mountable, said housing being adapted to allow access of micropollutants to the receiving phase through the diffusion limiting membrane.

43. A device according to claim 42, further comprising removable means for enabling water or conditioning liquid to be maintained in contact with the solid receiving phase between preparation and use of the device.

44. A device according t claim 43, wherein the housing and/or removable means comprises PTFE.

45. A passive sampling device for accumulating over a period of time micropollutants from an aquatic environment, which device comprises:
(a) a diffusion-limiting membrane contractable in use with the aquatic environment and adapted to allow rate-limited diffusion therethrough of the micropollutants; and
(b) a receiving phase having a sufficiently high affinity for the micropollutants for accumulating the micropollutants;
wherein the receiving phase is:
(i) a removable unitary element;
(ii) separated from the aquatic environment by said membrane;
(iii) comprised of a solid phase material immobilised by being bound in or to a hydrophobic solid support,
and wherein the diffusion-limiting membrane comprises pores traversing the membrane in a direction substantially at right angles to the plane of the membrane and having a diameter in the range of from 0.1 to 10 μm.

46. A device according to claim 45, wherein the solid support is in the form of a solid carrier for the solid phase material, which does not contain or retain water within its structure and can not exchange water with its environment, whereby the solid support is not subject to loss of water and hence changes in dimension, due either to evaporation or osmotic efflux.

47. A device according to claim 45, wherein the diffusion-limiting membrane comprises a solid, hydrophobic material, which contains less than 1% water and/or is substantially non-porous, whereby the diffusion pathway comprises the solid polymer itself and not any water contained therein.

48. A device according to claim 45, suitable for accumulating polar, organic micropollutants, wherein the membrane is selected from polysulphone, polycarbonate, cellulose dialysis membrane, PTFE, PVDF and glass fibre.

49. A device according to claim 45, suitable for accumulating inorganic micropollutants, wherein the membrane is selected from cellulose acetate, glass fibre membranes, nylon membranes and dialysis membranes.

50. A device according to claim 45, wherein the diffusion-limiting membrane is or is associated with molecular charge selective material.

51. A device according to claim 50, wherein the molecular charge selective material is selected from poly(4-vinylpyridine), poly(2,6-dimethylphenol) and perfluorinated polymers having pendant sulphonic acid groups.

52. A device according to claim 45, wherein the thickness of the membrane, and therefore diffusion pathway, is in the range of from 0.02 to 0.15 mm.

53. A device according to claim 52, wherein the thickness of the membrane, and therefore diffusion pathway, is less than 0.1 mm.

54. A device according to claim 45, wherein the thickness of the receiving phase is less than 1 mm.

55. A device according to claim 45, wherein the solid receiving phase is in the form of a cartridge or disk.

56. A device according to claim 45, wherein the immobilised solid phase material comprises $C_8$ to $C_{18}$ chain length hydrocarbon groups bonded in a silica-based polymer.

57. A device according to claim 45, wherein the solid support comprises a matrix of fibres.

58. A device according to claim 57, wherein the matrix of fibres comprises hydrophobic fibers.

59. A device according to claim 45, wherein a face of the membrane remote from the receiving phase is provided with netting or a mesh.

60. A device according to claim 45, further comprising an inert housing in which said receiving phase and said diffusion limiting membrane are removably mountable, said housing being adapted to allow access of micropollutants to the receiving phase through the diffusion limiting membrane.

61. A device according to claim 60, further comprising removable means for enabling water or conditioning liquid to be maintained in contact with the solid receiving phase between preparation and use of the device.

62. A device according to claim 61, wherein the housing and/or removable means comprises PTFE.

63. A device for monitoring micropollutants in an aquatic environment, which device comprises:
 (a) a diffusion-limiting membrane capable of being in contact with the aqueous environment when the device is in use and adapted to allow rate-limited diffusion therethrough of the micropollutants; and
 (b) a receiving phase being separated from the aqueous environment by the membrane and having a sufficiently high affinity for the micropollutants for receiving and retaining the micropollutants;
 wherein the receiving phase comprises an immobilised solid phase material supported by a solid support and wherein the diffusion-limiting membrane is or is associated with a molecular charge selective material selected from poly(4-vinylpyridine), poly(2,6-dimethylphenol) and perfluorinated polymers having pendant sulphonic acid groups.

64. A method for monitoring micropollutants in a polluted environment, which method comprises:
 (a) providing a receiving phase comprising an immobilised solid phase material for the micropollutants, which material is supported by a solid support;
 (b) providing a diffusion-limiting membrane adapted to allow rate-limited diffusion therethrough of the micropollutants and, in use, adapted to separate the receiving phase from the polluted environment;
 (c) bringing the membrane into contact with the polluted environment for a sufficient period of time to allow the micropollutants to collect in the immobilised solid phase material;
 (d) removing the solid receiving phase form the environment; and
 (e) analysing the micropollutants accumulated in the receiving phase, which further comprises pre-treating the receiving phase by coating or impregnating it with a photometric agent selected from bathocuproine, methylthymol blue, xylenol orange, glycine cresol red, binchinonic acid and 1,5-diphenyl carbohydrazide.

65. A device for monitoring non-polar, organic micropollutants in an aquatic environment, which device comprises:
 (a) a diffusion-limiting membrane capable of being in contact with the aqueous environment when the device is in use and adapted to allow rate-limited diffusion therethrough of the micropollutants; and
 (b) a receiving phase being separated from the aqueous environment by the membrane and having a sufficiently high affinity for the micropollutants for receiving and retaining the micropollutants
 wherein the receiving phase comprises an immobilised solid phase material and the diffusion-limiting membrane comprises a solid, hydrophobic polymeric material capable of determining rate of diffusion of the micropollutants therethrough which is or is associated with a molecular charge selective material selected from poly(4-vinylpyridine), poly(2,6-dimethylphenol) and perfluorinated polymers having pendant sulphonic acid groups.

66. A device suitable for monitoring inorganic micropollutants in an aquatic environment, which device comprises:
 (a) a diffusion-limiting membrane capable of being in contact with the aqueous environment when the device is in use and adapted to allow rate-limited diffusion therethrough of the micropollutants; and
 (b) a receiving phase being separated from the aqueous environment by the membrane and having a sufficiently high affinity for the micropollutants for receiving and retaining the micropollutants;
 wherein the receiving phase comprises an immobilised solid phase material, and the diffusion-limiting membrane comprises pores traversing the membrane in a direction substantially at right angles to the plane of the membrane and having a diameter in the range of from 0.1 to 10 μm, and wherein the membrane is selected from cellulose acetate, glass fibre membranes, nylon membranes and dialysis membranes.

67. A device suitable for monitoring inorganic micropollutants in an aquatic environment, which device comprises:
 (a) a diffusion-limiting membrane capable of being in contact with the aqueous environment when the device is in use and adapted to allow rate-limited diffusion therethrough of the micropollutants; and
 (b) a receiving phase being separated from the aqueous environment by the membrane and having a sufficiently high affinity for the micropollutants for receiving and retaining the micropollutants;
 wherein the receiving phase comprises an immobilised solid phase material, and the diffusion-limiting membrane comprises pores traversing the membrane in a direction substantially at right angles to the plane of the membrane and having a diameter in the range of from 0.1 to 10 μm, and wherein the diffusion-limiting membrane is or is associated with a molecular charge selective material selected from poly(4-vinylpyridine), poly(2,6-dimethylphenol) and perfluorinated polymers having pendant sulphonic acid groups.

68. A method of monitoring micropollutants in an aquatic environment, comprising:
placing a passive sampling device in contact with the aquatic environment;
accumulating, in the passive sampling device, a quantity of the micropollutants from the aquatic environment; and
analyzing the quantity of micropollutants accumulated in the passive sampling device;
wherein the passive sampling device includes:
a hydrophobic support material comprising a matrix of fibres;
a solid phase material bound to the hydrophobic support material and configured with a sufficiently high affinity for the micropollutants in the aquatic environment to accumulate the quantity of micropollutants; and
a diffusion-limiting membrane configured to separate the aquatic environment from the solid phase material and to allow rate-limited diffusion therethrough of the quantity of micropollutants.

\* \* \* \* \*

UNITED STATES PATENT AND TRADEMARK OFFICE
CERTIFICATE OF CORRECTION

| | |
|---|---|
| PATENT NO. | : 7,059,206 B1 |
| APPLICATION NO. | :10/069351 |
| DATED | : June 13, 2006 |
| INVENTOR(S) | : Jenny Kingston et al. |

Page 1 of 1

It is certified that error appears in the above-identified patent and that said Letters Patent is hereby corrected as shown below:

On the Title Page, Item (57), in the Abstract, line 5, "forcontinuously" should read --for continuously--.

In claim 2, column 31, line 41, "can not" should read --cannot--.

In claim 27, column 33, line 30, "separated form" should read --separated from--.

In claim 28, column 33, line 42, "can not" should read --cannot--.

In claim 44, column 34, line 29, "according t" should read --according to--.

In claim 46, column 34, line 55, "can not" should read --cannot--.

In claim 64, column 36, line 7, "form" should read --from--.

Signed and Sealed this

Twenty-second Day of August, 2006

JON W. DUDAS
*Director of the United States Patent and Trademark Office*